US008584670B2

(12) United States Patent
Hyde et al.

(10) Patent No.: US 8,584,670 B2
(45) **Date of Patent: *Nov. 19, 2013**

(54) METHOD, COMPOSITION, AND SYSTEM TO CONTROL PH IN PULMONARY TISSUE OF A SUBJECT

(75) Inventors: Roderick A. Hyde, Redmond, WA (US); Muriel Y. Ishikawa, Livermore, CA (US); Jordin T. Kare, Seattle, WA (US); Dennis J. Rivet, Portsmouth, VA (US); Lowell L. Wood, Jr., Bellevue, WA (US); Victoria Y. H. Wood, Livermore, CA (US)

(73) Assignee: Invention Science Fund I, LLC, Bellevue, WA (US)

( * ) Notice: Subject to any disclaimer, the term of this patent is extended or adjusted under 35 U.S.C. 154(b) by 1239 days.

This patent is subject to a terminal disclaimer.

(21) Appl. No.: 12/319,654

(22) Filed: Jan. 8, 2009

(65) Prior Publication Data

US 2010/0078014 A1 Apr. 1, 2010

Related U.S. Application Data

(63) Continuation of application No. 12/286,753, filed on Sep. 30, 2008, which is a continuation-in-part of application No. 12/286,752, filed on Sep. 30, 2008, which is a continuation-in-part of application No. 12/286,729, filed on Sep. 30, 2008.

(51) Int. Cl.

| | |
|---|---|
| ***A61M 11/00*** | (2006.01) |
| ***A61M 13/00*** | (2006.01) |
| ***A61M 15/00*** | (2006.01) |
| ***A61K 9/00*** | (2006.01) |
| ***A61K 9/12*** | (2006.01) |
| ***A61K 9/14*** | (2006.01) |

(52) U.S. Cl.
USPC .................. 128/200.14; 128/200.24; 424/46; 424/489

(58) Field of Classification Search
USPC .................. 424/46, 489; 128/200.14, 200.24
See application file for complete search history.

(56) References Cited

U.S. PATENT DOCUMENTS 4,054,622 A * 10/1977 Lester .......................... 261/64.1
4,186,183 A 1/1980 Steck et al.
4,217,344 A 8/1980 Vanlerberghe et al.
4,235,871 A 11/1980 Papahadjopoulos et al.
4,261,975 A 4/1981 Fullerton et al.
4,485,054 A 11/1984 Mezei et al.
4,501,728 A 2/1985 Geho et al.
4,774,085 A 9/1988 Fidler
4,789,633 A 12/1988 Huang et al.
4,837,028 A 6/1989 Allen
4,895,719 A 1/1990 Radhakrishnan et al.
4,946,787 A 8/1990 Eppstein et al.
5,049,388 A 9/1991 Knight et al.
5,192,528 A * 3/1993 Radhakrishnan et al. ...... 424/45
5,628,981 A 5/1997 Liversidge et al.
5,786,214 A 7/1998 Holmberg
5,965,434 A 10/1999 Wolff et al.
6,080,791 A 6/2000 Bodian et al.
6,132,893 A 10/2000 Schöning et al.
6,143,420 A 11/2000 Heimann et al.
6,187,332 B1 2/2001 Gern et al.
6,197,835 B1 3/2001 Gañan-Cálvo
6,267,310 B1 7/2001 Cappola
6,301,247 B1 10/2001 Larson et al.
6,426,086 B1 7/2002 Papahadjopoulos et al.
6,464,940 B1 10/2002 Akioka et al.
6,466,133 B1 10/2002 Skardon
6,504,841 B1 1/2003 Larson et al.
6,596,305 B1 7/2003 Edgerly-Plug
6,716,636 B1 4/2004 Schneider et al.
6,897,196 B1 5/2005 Szoka, Jr. et al.
7,009,169 B2 3/2006 Wong et al.
7,119,900 B2 10/2006 Okumura et al.
7,181,345 B2 2/2007 Rosenfeld et al.
7,208,314 B2 4/2007 Monahan et al.
7,213,465 B2 5/2007 Benzel et al.
7,229,973 B2 6/2007 Bae et al.
RE39,871 E 10/2007 Skardon
7,285,243 B2 10/2007 Springston et al.
7,334,845 B2 2/2008 Peterson et al.
7,348,453 B2 3/2008 Rozema et al.
7,383,071 B1 6/2008 Russell et al.

(Continued)

FOREIGN PATENT DOCUMENTS

WO WO 99/30087 * 6/1999

OTHER PUBLICATIONS

Arunabh and Edasery "Human Immunodeficiency Virus and Primary Pulmonary Hypertension," Western Journal of Medicine Dec. 1993, 159(6), pp. 708-709.*
Auguste et al.; "Triggered release of siRNA from poly(ethylene glycol)-protected, pH-dependent liposomes"; Journal of Controlled Release; 2008; pp. 266-274; vol. 130; Elsevier B.V.
Brabec et al.; "Conformational Changes, Plasma Membrane Penetration, and Infection by Human Rhinovirus Type 2: Role of Receptors and Low pH"; Journal of Virology; May 2003; pp. 5370-5377; vol. 77, No. 9; American Society for Microbiology.
Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

(Continued)

*Primary Examiner* — James H Alstrum Acevedo
(74) *Attorney, Agent, or Firm* — Dorsey & Whitney LLP

(57) ABSTRACT

Methods, pharmaceutical compositions, and systems are provided which include a method for treating a pulmonary viral infectious disease in a subject. The method includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

51 Claims, 15 Drawing Sheets

(56) References Cited

U.S. PATENT DOCUMENTS

| | | | | |
|---|---|---|---|---|
| 7,682,920 | B2 | 3/2010 | Herner | |
| 2003/0075172 | A1 | 4/2003 | Johnson et al. | |
| 2005/0065448 | A1 | 3/2005 | Stahmann et al. | |
| 2005/0209526 | A1 | 9/2005 | Ingley, III et al. | |
| 2006/0122863 | A1 | 6/2006 | Gottesman et al. | |
| 2007/0057077 | A1 | 3/2007 | Huang | |
| 2007/0068810 | A1 | 3/2007 | Tsukashima et al. | |
| 2007/0088334 | A1 | 4/2007 | Hillis et al. | |
| 2007/0106138 | A1 | 5/2007 | Beiski et al. | |
| 2007/0134166 | A1 | 6/2007 | Hunt et al. | |
| 2007/0167843 | A1 | 7/2007 | Cho et al. | |
| 2008/0000473 | A1 | 1/2008 | Stephenson et al. | |
| 2008/0024323 | A1 | 1/2008 | Kadaba | |
| 2008/0045156 | A1 | 2/2008 | Sakhpara | |
| 2008/0138351 | A1 | 6/2008 | Dwek et al. | |
| 2009/0196930 | A1* | 8/2009 | Surber et al. | 424/489 |
| 2010/0081954 | A1 | 4/2010 | Hyde et al. | |

OTHER PUBLICATIONS

Carraro et al.; "*S*-nitrosothiols regulate cell-surface pH buffering by airway epithelial cells during the human immune response to rhinovirus"; American Journal of Physiology—Lung Cellular and Molecular Physiology; May 2006; pp. L827-L832; vol. 290; American Physiological Society.

Chauhan et al.; "Air pollution and infection in respiratory illness"; British Medical Bulletin; 2003; pp. 95-112; vol. 68; The British Council 2003.

Chen et al.; "Real-time RT-PCR for H5N1 avian influenza A virus detection"; Journal of Medical Microbiology; 2007; pp. 603-607; vol. 56; SGM.

Deamer et al.; "Large Volume Liposomes by an Ether Vaporization Method"; BBA; 1976; pp. 629-634; vol. 443; Elsevier Scientific Publishing Company, Amsterdam.

Fraley et al.; "Entrapment of a bacterial plasmid in phospholipid vesicles: Potential for gene transfer"; Proceedings of the National Academy of Sciences—Cell Biology; Jul. 1979; pp. 3348-3352; vol. 76, No. 7.

Gern et al.; "Inhibition of Rhinovirus Replication In Vitro and In Vivo by Acid-Buffered Saline"; The Journal of Infectious Diseases; Apr. 15, 2007; pp. 1137-1143; vol. 195; Infectious Diseases Society of America.

Gupta et al.; "Single virus particle mass detection using microresonators with nanoscale thickness"; Applied Physics Letters; Mar. 15, 2004; pp. 1976-1978; vol. 84, No. 11; American Institute of Physics.

Hermann et al.; "Optimization of a Sampling System for Recovery and Detection of Airborne Porcine Reproductive and Respiratory Syndrome Virus and Swine Influenza Virus"; Applied and Environmental Microbiology; Jul. 2006; pp. 4811-4818; vol. 72, No. 7; American Society for Microbiology.

Hollingsworth et al.; "Ozone and Pulmonary Innate Immunity"; Proceedings of the American Thoracic Society; 2007; pp. 240-246; vol. 4.

Hope et al.; "Production of large unilamellar vesicles by a rapid extrusion procedure. Characterization of size distribution, trapped volume and ability to maintain a membrane potential"; BBA; 1985; pp. 55-65; vol. 812; Elsevier Science Publishers B.V.

Ilyushina et al.; "Contribution of H7 haemagglutinin to amantadine resistance and infectivity of influenza virus"; Journal of General Virology; 2007; pp. 1266-1274; vol. 88; SGM.

Jeon et al.; "A DNA Aptamer Prevents Influenza Infection by Blocking the Receptor Binding Region of the Viral Hemagglutinin"; The Journal of Biological Chemistry; Nov. 12, 2004; pp. 48410-48419; vol. 279, No. 46; The American Society for Biochemistry and Molecular Biology, Inc.

Kostikas et al.; "pH in Expired Breath Condensate of Patients with Inflammatory Airway Diseases"; American Journal of Respiratory and Critical Care Medicine; 2002; pp. 1364-1370; vol. 165.

Kuhrt et al.; "Virucidal Activity of Glutaric Acid and Evidence for Dual Mechanism of Action"; Antimicrobial Agents and Chemotherapy; Dec. 1984; pp. 924-927; vol. 26, No. 6; American Society for Microbiology.

Labiris et al.; "Pulmonary drug delivery. Part I: Physiological factors affecting therapeutic effectiveness of aerosolized medications"; British Journal of Clinical Pharmacology; 2003; pp. 588-599; vol. 56; Blackwell Publishing Ltd.

Labiris et al.; "Pulmonary drug delivery. Part II: The role of inhalant delivery devices and drug formulations in therapeutic effectiveness of aerosolized medications"; British Journal of Clinical Pharmacology; 2003; pp. 600-612; vol. 56; Blackwell Publishing Ltd.

Matrosovich et al.; "Human and avian influenza viruses target different cell types in cultures of human airway epithelium"; PNAS; Mar. 30, 2004; pp. 4620-4624; vol. 101, No. 13; The National Academy of Sciences of the USA.

Myatt et al.; "Airborne rhinovirus detection and effect of ultraviolet irradiation on detection by a semi-nested RT-PCR assay"; BMC Public Health; 2003; pp. 1-7; vol. 3, No. 5; Myatt et al.

Prchla et al.; "Uncoating of Human Rhinovirus Serotype 2 from Late Endosomes"; Journal of Virology; Jun. 1994; pp. 3713-3723; vol. 68, No. 6; American Society for Microbiology.

Proske et al.; "Aptamers-basic research, drug development, and clinical applications"; Applied Microbiology and Biotechnology; 2005; pp. 367-374; vol. 69; Springer-Verlag 2005.

Renneisen et al.; "Inhibition of Expression of Human Immunodeficiency Virus-1 in Vitro by Antibody-targeted Liposomes Containing Antisense RNA to the env Region"; Sep. 25, 1990; pp. 16337-16342; vol. 265, No. 27; The American Society for Biochemistry and Molecular Biology, Inc.

Rennie et al.; "Low pH gel intranasal sprays inactivate influenza viruses in vitro and protect ferrets against influenza infection"; Respiratory Research; 2007; pp. 1-7; vol. 8, No. 38; Rennie et al.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Statheropoulos et al.; "Vegetation Fire Smoke: Nature, Impacts and Policies to Reduce Negative Consequences on Humans and the Environment"; European and Mediterranean Major Hazards Agreement; May 30, 2007; pp. 1-36; Council of Europe.

Straubinger et al.; "pH-sensitive liposomes mediate cytoplasmic delivery of encapsulated macromolecules"; Federation of European Biochemical Societies; Jan. 1985; pp. 148-154; vol. 179, No. 1; Elsevier Science Publishers B.V.

Szoka, Jr. et al.; "Comparative Properties and Methods of Preparation of Lipid Vesicles (Liposomes)"; Annual Review of Biophysics and Bioengineering; 1980; pp. 467-508; vol. 9; Annual Reviews Inc.

Takeda et al.; "Influenza A Virus $M_2$ Ion Channel Activity Is Essential for Efficient Replication in Tissue Culture"; Journal of Virology; Feb. 2002; pp. 1391-1399; vol. 76, No. 3; American Society for Microbiology.

Tanaka et al.; "Acid fog and hospital visits for asthma: an epidemiological study"; European Respiratory Journal; 1998; pp. 1301-1306; vol. 11; ERS Journals Ltd 1998.

Uiprasertkul et al.; "Influenza A H5N1 Replication Sites in Humans"; Emerging Infectious Diseases; Jul. 2005; pp. 1036-1041; vol. 11, No. 7.

Vorauer-Uhl et al.; "Determination of Liposome Size Distribution by Flow Cytometry"; Cytometry; 2000; pp. 166-171; vol. 39; Wiley-Liss, Inc.

Whiteman et al.; "Human Rhinovirus Selectivity Modulates Membranous and Soluble Forms of Its Intercellular Adhesion Molecule-1 (ICAM-1) Receptor to Promote Epithelial Cell Infectivity"; The Journal of Biological Chemistry; Apr. 4, 2003; pp. 11954-11961; vol. 278, No. 14; The American Society for Biochemistry and Molecular Biology, Inc.

Williams et al.; "Low density lipoprotein receptor-independent hepatic uptake of a synthetic, cholesterol-scavenging lipoprotein: Implications for the treatment of receptor-deficient atherosclerosis"; Proceedings of the National Academy of Sciences; Jan. 1988; pp. 242-246; vol. 85.

(56) References Cited

OTHER PUBLICATIONS

Burden, Allyson; "NES Integrator—Glossary"; S-A-H Services; located at: www.sahservices.com/nes_provision/new_integrator_-_glossary; printed on Sep. 28, 2011; pp. 1-10.
Holma, Bo; "Effects of Inhaled Acids on Airway Mucus and Its Consequences for Health"; Environmental Health Perspectives; 1989; pp. 109-113; vol. 79.
New York State Consensus Asthma Guideline Expert Panel; "Clinical Guideline for the Diagnosis, Evaluation, and Management of Adults and Children with Asthma—2005"; accessed at www.health.state.ny.us/diseases/asthma/pdf/2005_asthma_guidelines.pdf on Oct. 2, 2011.
Beers et al.; "The Merck Manual of Diagnosis and Therapy (Seventeenth Edition)"; bearing a date of 1999; pp. 556-569 and one cover page; Section 6; Merck Research Laboratories: Division of Merck & Co., Inc.
Lee et al.; "Polymer-caged liposomes: a pH-responsive delivery system with high stability"; J. Am. Chem. Soc.; Dec. 12, 2007; pp. 15096-15097; Supporting Information (pp. pp. S1-S9); vol. 129, No. 49; Epub Nov. 14, 2007.

* cited by examiner

| A device including 701 | → | an aerosol generator, and a pharmaceutical composition including a membrane selective for a charged ion configured to achieve a selected pH of a pulmonary tissue in a subject  702 |

700

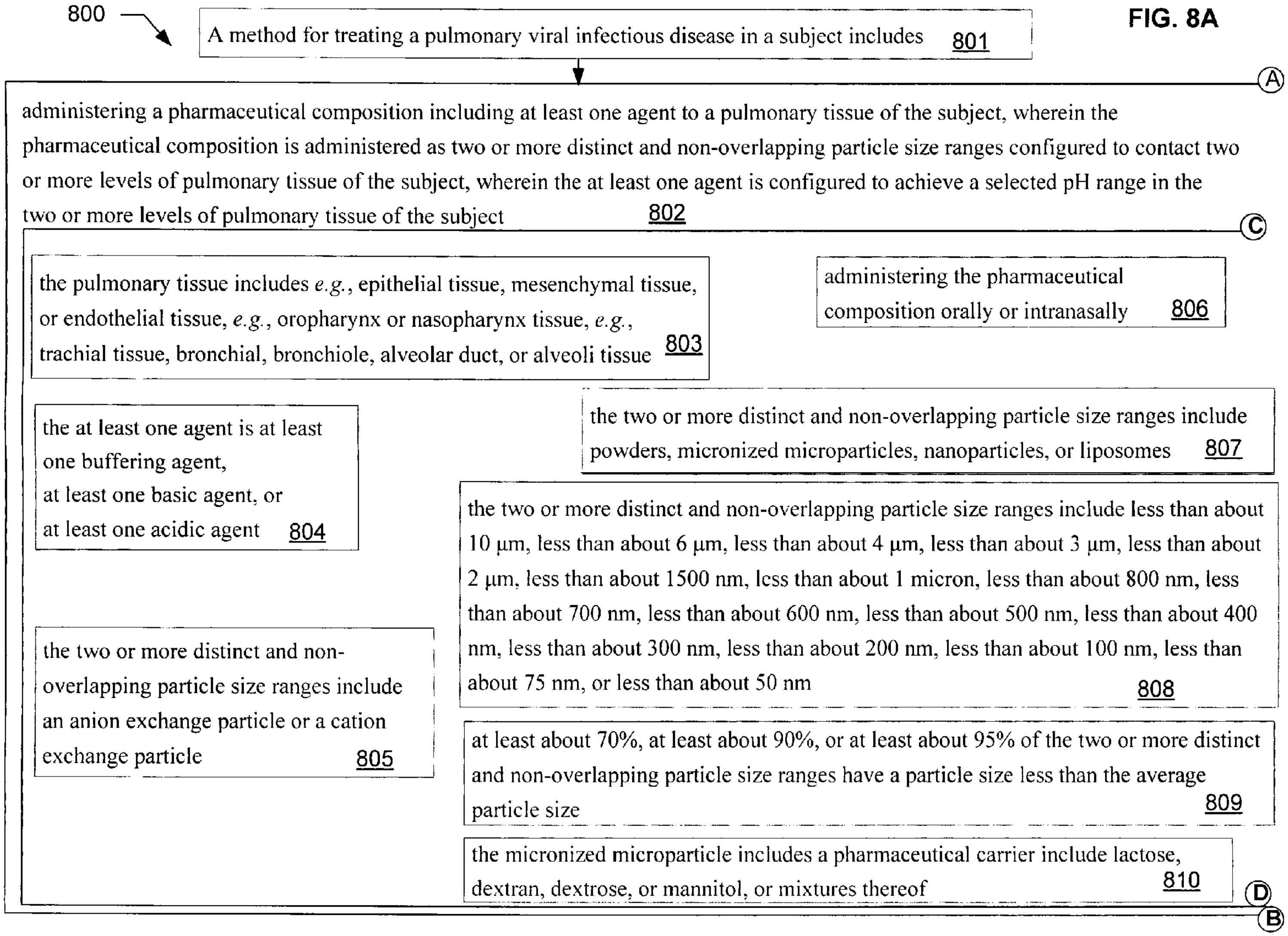

FIG. 8A

800 →  801  A method for treating a pulmonary viral infectious disease in a subject includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the

METHOD, COMPOSITION, AND SYSTEM TO CONTROL PH IN PULMONARY TISSUE OF A SUBJECT

RELATED APPLICATIONS

For purposes of the USPTO extra-statutory requirements, the present application constitutes a continuation of U.S. patent application Ser. No. 12/286,753, entitled METHOD, COMPOSITION, AND SYSTEM TO CONTROL PH IN PULMONARY TISSUE OF A SUBJECT, naming Roderick A. Hyde, Muriel Y. Ishikawa, Jordin T. Kare, Dennis J. Rivet, Lowell L. Wood, Jr. and Victoria Y. H. Wood as inventors, filed 30 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/286,752, entitled METHOD, DEVICE, AND SYSTEM TO CONTROL PH IN PULMONARY TISSUE OF A SUBJECT, naming Roderick A. Hyde, Muriel Y. Ishikawa, Jordin T. Kare, Dennis J. Rivet, Lowell L. Wood, Jr. and Victoria Y. H. Wood as inventors, filed 30 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/286,729, entitled METHOD, DEVICE, AND SYSTEM TO CONTROL PH IN PULMONARY TISSUE OF A SUBJECT, naming Roderick A. Hyde, Muriel Y. Ishikawa, Jordin T. Kare, Dennis J. Rivet, Lowell L. Wood, Jr. and Victoria Y. H. Wood as inventors, filed 30 Sep. 2008, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Methods, pharmaceutical compositions, and systems are described herein which include a method for treating a pulmonary viral infectious disease in a subject. The method includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject. The at least one agent includes, but is not limited to, at least one buffering agent, at least one basic agent, or at least one acidic agent, or a combination thereof. The levels of pulmonary tissue include, but are not limited to, oropharynx tissue, nasopharynx tissue, trachial tissue, bronchial, bronchiole, alveolar duct, or alveoli tissue. The pulmonary tissue includes epithelial tissue, mesenchymal tissue, or endothelial tissue. The two or more distinct and non-overlapping particle size ranges include, but are not limited to, powders, micronized microparticles, nanoparticles, or liposomes. The two or more distinct and non-overlapping particle size ranges include, but are not limited to, less than about 10 μm, less than about 6 μm, less than about 4 μm, less than about 3 μm, less than about 2 μm, less than about 1500 nm, less than about 1 μm, less than about 800 nm, less than about 700 nm, less than about 600 nm, less than about 500 nm, less than about 400 nm, less than about 300 nm, less than about 200 nm, less than about 100 nm, less than about 75 nm, or less than about 50 nm. The two or more distinct and non-overlapping particle size ranges include, but are not limited to, less than about 1900 nm, less than about 1800 mm, less than about 1700 nm, less than about 1600 nm, less than about 1500 nm, less than about 1400 nm, less than about 1300 mm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm. In the method described herein, at least about 70%, at least about 90%, or at least about 95% of the two or more distinct and non-overlapping particle size ranges may have a particle size less than the average particle size. The micronized microparticle includes a pharmaceutical carrier which includes, but is not limited to, lactose, dextran, dextrose, or mannitol, or mixtures thereof.

The method further includes administering the pharmaceutical composition which may include a first agent in first-sized particles configured to maintain a first pH range in a first level of pulmonary tissue of the subject, and a second agent in second-sized particles configured to maintain a second pH range in a second level of pulmonary tissue of the subject. The pharmaceutical composition is administered in response to a sensed environmental condition wherein the sensed environmental condition includes a potentially infectious environment. The first-sized particles and the second-sized particles include the two or more particle size ranges which include, but are not limited to, of less than about 10 μm, less than about 6 μm, less than about 4 μm, or less than about 2 μm. The first agent may include a buffering agent to maintain the first pH range below approximately 7.0. The first agent may be a buffering agent configured to maintain the first pH range from approximately 7.2 to approximately 7.6. The second agent may be a buffering agent configured to maintain the second pH range from approximately 6.4 to approximately 7.4. The pharmaceutical composition may be administered in response to a sensed environmental condition. The sensed environmental condition includes a potentially infectious environment. The method as described therein may further comprise administering the pharmaceutical composition orally or intranasally. The pharmaceutical composition may be configured to provide a timed-release of the buffering agents. The pharmaceutical composition may be configured to provide a slow-absorbing form of the buffering agents. In one aspect, the at least one buffering agent is linked to a viral homing entity. In a further aspect, the viral homing entity binds to a surface molecule of the virus. The viral homing entity may bind to a cell or tissue of the subject. The buffering agent includes, but is not limited to, phosphate buffer, citrate buffer, lactate buffer, pyruvate buffer, or an organic acid buffer.

The method may further include a sensor is configured to monitor a condition of the subject. the sensor is configured to monitor at least one of pH of the pulmonary tissue, pH of an exhalant humidity of an exhalant, temperature, breathing rate, peak rate of exhalation, tidal volume, vital capacity, inspiratory capacity, expiratory reserve volume, or residual volume. The method may further include a controller responsive to the sensor configured to alter the selected pH range in the two or more levels of pulmonary tissue of the subject. The monitoring sensor is in an airway passage of the subject. The monitoring sensor is in a sinus or a nostril of the subject. The method as described therein may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The pharmaceutical composition including the at least one agent can be administered in response to information from the pH-sensitive detection component. The subject may be mammalian or avian.

Pharmaceutical compositions are described herein which include at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject. The levels of pulmonary tissue include, but are not limited to, oropharynx tissue, nasopharynx tissue, trachial tissue, bronchial, bronchiole, alveolar duct, or alveoli tissue. The pulmonary tissue includes epithelial tissue, mesenchymal tissue, or endothelial tissue. The at least one agent may include at least one buffering agent. The at least one agent may include at least one basic agent. The at least one agent may include at least one acidic agent. The pharmaceutical composition may include a first agent in first-sized particles configured to maintain a first pH range in a first level of pulmonary tissue of the subject, and a second agent in second-sized particles configured to maintain a second pH range in a second level of pulmonary tissue of the subject. The pharmaceutical composition is administered in response to a sensed environmental condition wherein the sensed environmental condition includes a potentially infectious environment. The first-sized particles and the second-sized particles include the two or more particle size ranges which include, but are not limited to, of less than about 10 μm, less than about 6 μm, less than about 4 μm, or less than about 2 μm. The at least one of the first-sized particles and the second-sized particles have the particle size ranges including, but not limited to, less than about 4 μm, less than about 3 μm, less than about 2 μm, less than about 1500 nm, less than about 1 micron, less than about 800 nm, less than about 700 nm, less than about 600 nm, less than about 500 nm, less than about 400 nm, less than about 300 nm, less than about 200 nm, less than about 100 nm, less than about 75 nm, or less than about 50 nm. The at least one of the first-sized particles and the second-sized particles may have the particle size including, but not limited to, less than about 1900 nm, less than about 1800 nm, less than about 1700 nm, less than about 1600 nm, less than about 1500 nm, less than about 1400 nm, less than about 1300 mm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm. The first agent may include a buffering agent to maintain the first pH range below approximately 7.0. The first agent may be a buffering agent configured to maintain the first pH range from approximately 7.2 to approximately 7.6. The second agent may be a buffering agent configured to maintain the second pH range from approximately 6.4 to approximately 7.4. The pharmaceutical composition may be administered in response to a sensed environmental condition. The sensed environmental condition includes a potentially infectious environment. The pharmaceutical composition as described therein may further comprise administering the pharmaceutical composition orally or intranasally. The pharmaceutical composition may be configured to provide a timed-release of the buffering agents. The pharmaceutical composition may be configured to provide a slow-absorbing form of the buffering agents. In one aspect, the at least one buffering agent is linked to a viral homing entity. In a further aspect, the viral homing entity binds to a surface molecule of the virus. The viral homing entity may bind to a cell or tissue of the subject. The buffering agent includes, but is not limited to, phosphate buffer, citrate buffer, lactate buffer, pyruvate buffer, or an organic acid buffer. The composition may further include a sensor is configured to monitor a condition of the subject. the sensor is configured to monitor at least one of pH of the pulmonary tissue, pH of an exhalant humidity of an exhalant, temperature, breathing rate, peak rate of exhalation, tidal volume, vital capacity, inspiratory capacity, expiratory reserve volume, or residual volume. The composition may further include a controller responsive to the sensor configured to alter the selected pH range in the two or more levels of pulmonary tissue of the subject. The monitoring sensor is in an airway passage of the subject. The monitoring sensor is in a sinus or a nostril of the subject. The composition as described therein may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The pharmaceutical composition including the at least one agent can be administered in response to information from the pH-sensitive detection component. The subject may be mammalian or avian.

Systems are described herein which include an aerosol generator and a pharmaceutical composition including at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject. A device may encompass the system as provided herein. The at least one agent includes, but is not limited to, at least one buffering agent, at least one basic agent, or at least one acidic agent, or a combination thereof. The levels of pulmonary tissue include, but are not limited to, oropharynx tissue, nasopharynx tissue, trachial tissue, bronchial, bronchiole, alveolar duct, or alveoli tissue. The pulmonary tissue includes epithelial tissue, mesenchymal tissue, or endothelial tissue. The two or more distinct and non-overlapping particle size ranges include, but are not limited to, less than about 10 μm, less than about 6 μm, less than about 4 μm, less than about 3 μm, less than about 2 μm, less than about 1500 nm, less than about 1 μm, less than about 800 nm, less than about 700 nm, less than about 600 nm, less than about 500 nm, less than about 400 nm, less than about 300 nm, less than about 200 nm, less than about 100 nm, less than about 75 nm, or less than about 50 nm. The system further includes administering the pharmaceutical composition which may include a first agent in first-sized particles configured to maintain a first pH range in a first level of pulmonary tissue of the subject, and a second agent in second-sized particles configured to maintain a second pH range in a second level of pulmonary tissue of the subject. The pharmaceutical composition is administered in response to a sensed environmental condition wherein the sensed environmental condition includes a potentially infectious environment. The first-sized particles and the second-sized particles include the two or more particle size ranges which include, but are not limited to, of less than about 10 μm, less than about 6 μm, less than about 4 μm, or less than about 2 μm. The first agent may include a buffering agent to maintain the first pH range below approximately 7.0. The first agent may be a buffering agent configured to maintain the first pH range from approximately 7.2 to approximately 7.6. The second agent may be a buffering agent configured to maintain the second pH range from approximately 6.4 to approximately 7.4. The pharmaceutical composition may be administered in response to a sensed environmental condition. The sensed environmental condition includes a potentially infectious environment. The system as described therein may further comprise administering the pharmaceutical composition orally or intranasally. In one aspect, the at least one buffering agent is linked to a viral homing entity. In a further aspect, the viral homing entity binds to a surface molecule of the virus. The viral homing entity may bind to a cell or tissue of the subject. The buffering agent includes, but is not limited to, phosphate buffer, citrate buffer, lactate buffer, pyruvate buffer, or an organic acid buffer. The system may include a device including the aerosol generator and the pharmaceutical composition. The charged ion includes a cation, e.g., $H^+$, $K^+$, or $Mg^{2+}$. The charged ion includes an anion, e.g., phosphate, citrate, lactate, pyruvate, or an organic acid. The aerosol generator can be configured to administer the pharmaceutical composition to the pulmonary tissue of the subject. The system may further include a sensor is configured to monitor a condition of the subject. the sensor is configured to monitor at least one of pH of the pulmonary tissue, pH of an exhalant humidity of an exhalant, temperature, breathing rate, peak rate of exhalation, tidal volume, vital capacity, inspiratory capacity, expiratory reserve volume, or residual volume. The system may further include a controller responsive to the sensor configured to alter the selected pH range in the two or more levels of pulmonary tissue of the subject. The controller can be configured to deliver one or more particle size ranges of the selected pH. The monitoring sensor is in an airway passage of the subject. The monitoring sensor is in a sinus or a nostril of the subject. The monitoring sensor may be integral with the system. The system as described therein may further include a pH-sensitive detection component in the pharmaceutical composition, the pH-sensitive detection component configured to communicate to the pH-monitoring sensor. The pH-sensitive detection component may release a marker indicating a pH range, and the pH-monitoring sensor is configured to recognize the marker. The pharmaceutical composition including the at least one agent can be administered in response to information from the pH-sensitive detection component. The aerosol generator can administer a continuous or pulsatile dose of the pharmaceutical composition. The aerosol dose of the pharmaceutical composition can be delivered directly to an individual. The aerosol dose of the pharmaceutical composition can be delivered to one or more individuals in an enclosed space. The aerosol dose of the pharmaceutical composition may be delivered through a heating, ventilation, or air conditioning system. The pharmaceutical composition may be configured to provide a timed-release of the buffering agents. The pharmaceutical composition may be configured to provide a slow-absorbing form of the buffering agents. The pharmaceutical composition includes, but is not limited to, a liquid or a powder. The subject may be mammalian or avian.

A kit is described herein which includes a system including an aerosol generator, and a pharmaceutical composition including at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject. The kit further includes instructions for use.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 8A, 8B, 8C, and 8D depicts a logic flowchart of a method such as those depicted in FIGS. 1 and 2.

DETAILED DESCRIPTION

Figure 1A:
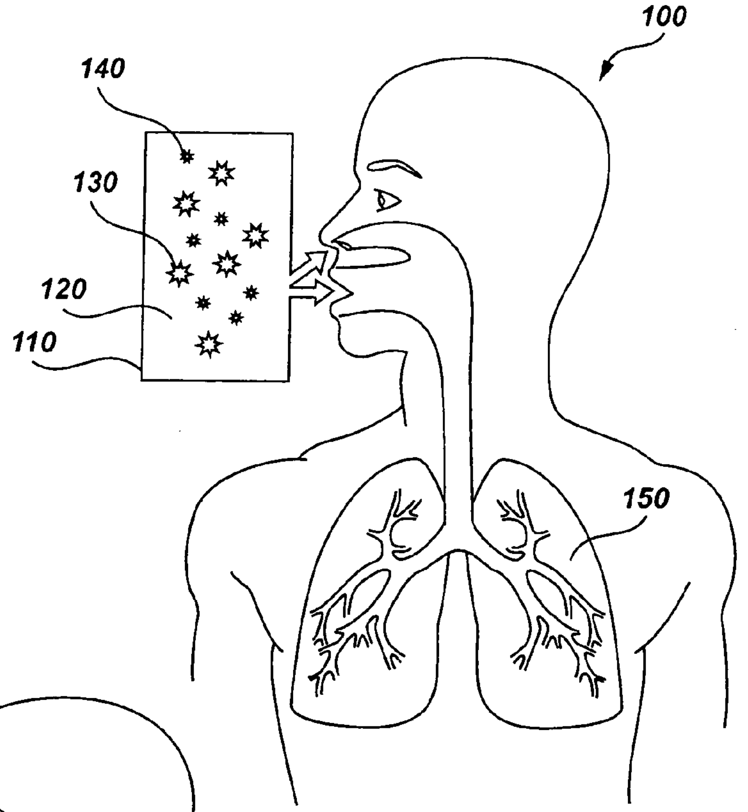
FIGS. 1A and 1B depict a diagrammatic view of one aspect of an exemplary embodiment of a method, device, or system that may serve as an illustrative environment for subject matter technologies.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Methods, pharmaceutical compositions, and systems are described herein which include a method for treating a pulmonary viral infectious disease in a subject. The method includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject. The at least one agent includes, but is not limited to, at least one buffering agent, at least one basic agent, or at least one acidic agent, or a combination thereof. The levels of pulmonary tissue include, but are not limited to, oropharynx tissue, nasopharynx tissue, trachial tissue, bronchial, bronchiole, alveolar duct, or alveoli tissue. The pulmonary tissue includes epithelial tissue, mesenchymal tissue, or endothelial tissue. The two or more distinct and non-overlapping particle size ranges include, but are not limited to, powders, micronized microparticles, nanoparticles, or liposomes. The pharmaceutical composition may include a first agent in first-sized particles configured to maintain a first pH range in a first level of pulmonary tissue of the subject, and a second agent in second-sized particles configured to maintain a second pH range in a second level of pulmonary tissue of the subject. The pharmaceutical composition is administered in response to a sensed environmental condition wherein the sensed environmental condition includes a potentially infectious environment. The method may further include a sensor is configured to monitor a condition of the subject. the sensor is configured to monitor at least one of pH of the pulmonary tissue, pH of an exhalant humidity of an exhalant, temperature, breathing rate, peak rate of exhalation, tidal volume, vital capacity, inspiratory capacity, expiratory reserve volume, or residual volume. The method may further include a controller responsive to the sensor configured to alter the selected pH range in the two or more levels of pulmonary tissue of the subject.

Pharmaceutical compositions are described herein which include at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject.

Systems are described herein which include an aerosol generator and a pharmaceutical composition including at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject. A device may encompass the system as provided herein.

With reference to the figures, and with reference now to FIGS. 1 through 8, depicted is one aspect of a system that may serve as an illustrative environment of and/or for subject matter technologies, for example, a method comprising receiving data including data of a physical condition affecting one or more subjects, the data informing administration of a pharmaceutical composition in response to the physical condition, wherein the pharmaceutical composition is configured to contact pulmonary tissue to treat a pulmonary disease or condition in the one or more subjects; or a method for treating a pulmonary viral infectious disease in a subject comprising administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject; or a device comprising an aerosol generator and a pharmaceutical composition including a membrane selective for a charged ion configured to achieve a selected pH of a pulmonary tissue in a subject. Accordingly, the present application first describes certain specific exemplary methods of FIGS. 1 through 8; thereafter, the present application illustrates certain specific exemplary methods. Those having skill in the art will appreciate that the specific methods described herein are intended as merely illustrative of their more general counterparts.

Figure 1B:
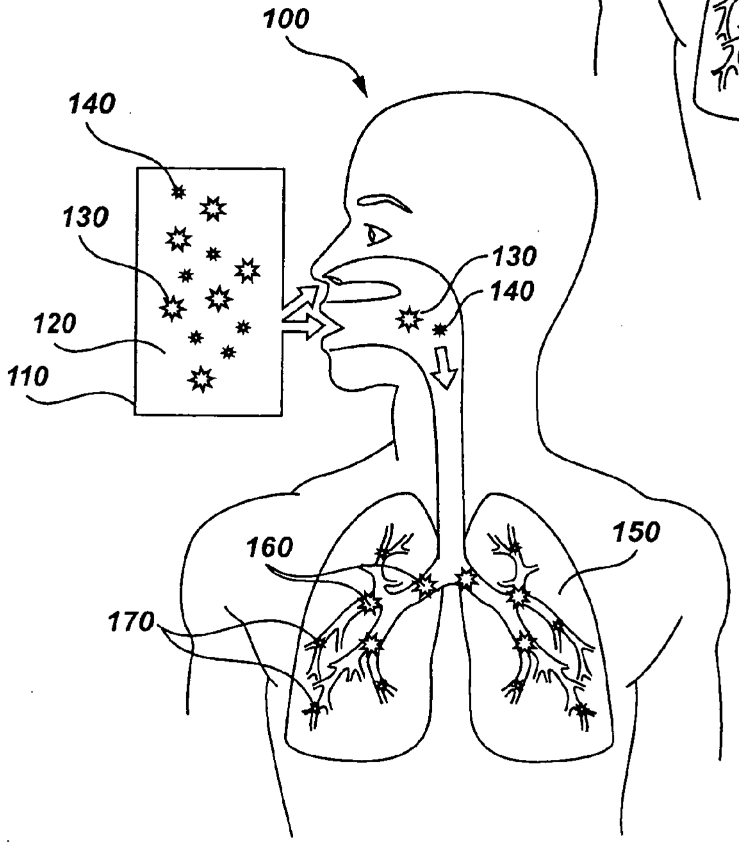

Continuing to refer to FIG. 1, depicted is a partial diagrammatic view of an illustrative embodiment of a method for treating a pulmonary viral infectious disease in a subject or a device 110 for use with the method. In FIG. 1A, a method for treating a pulmonary viral infectious disease in a subject 100 includes administering a pharmaceutical composition 120 including at least one agent 130, 140 to a pulmonary tissue of the subject, wherein the pharmaceutical composition is administered as two or more distinct and non-overlapping particle size ranges 130, 140 configured to contact two or more levels 160, 170 of pulmonary tissue 150 of the subject, In FIG. 1B, the method includes administering a pharmaceutical composition 120 including at least one agent 130, 140 to a pulmonary tissue 150 of the subject, wherein the pharmaceutical composition is administered as two or more distinct and non-overlapping particle size ranges 130, 140, wherein the at least one agent is configured to achieve a selected pH range in the two or more levels 160, 170 of pulmonary tissue 150 of the subject. The two or more distinct and non-overlapping particle size ranges 130, 140, may be configured to achieve a selected pH range in the two or more levels, for example, in the bronchus or bronchi 160 of the lungs, or further into the bronchial tree 170 towards the bronchi, bronchioles, alveolar duct, or alveoli of the lungs of the subject.

Figure 2A:
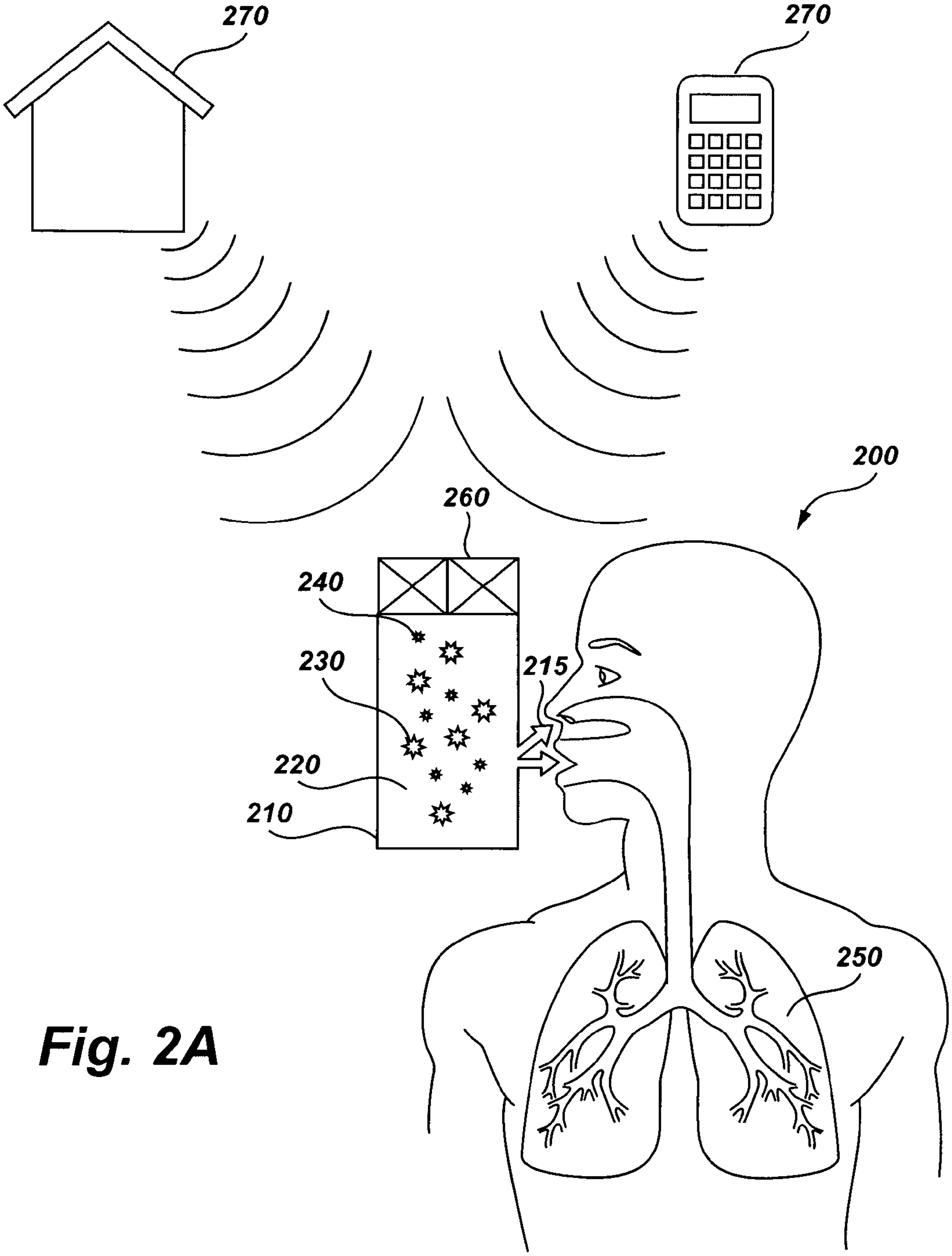
FIGS. 2A, 2B, and 2C depict a diagrammatic view of one aspect of an exemplary embodiment of a method, device, or system that may serve as an illustrative environment for subject matter technologies.
Figure 2B:
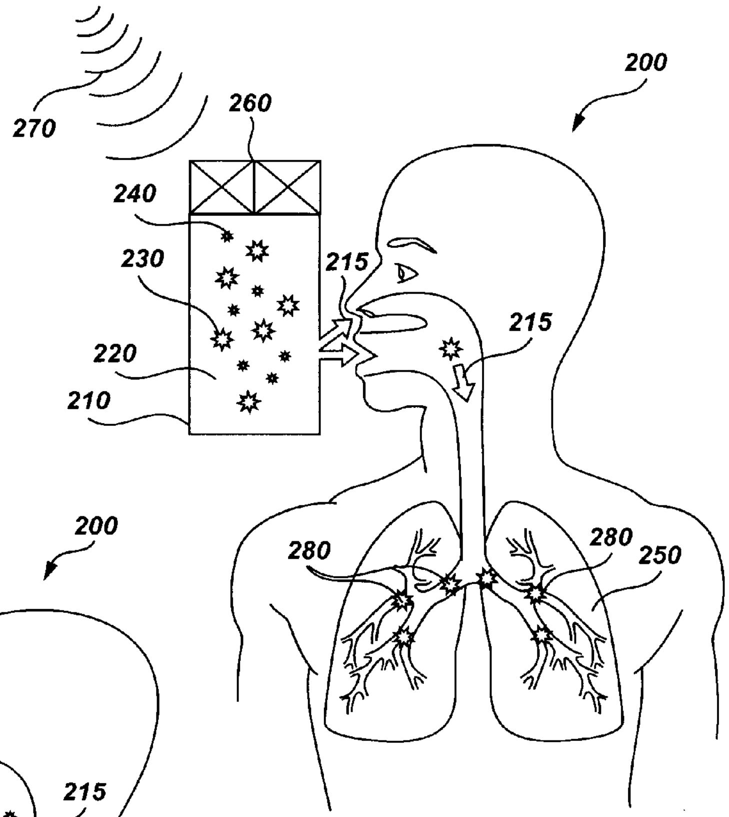
Figure 2C:
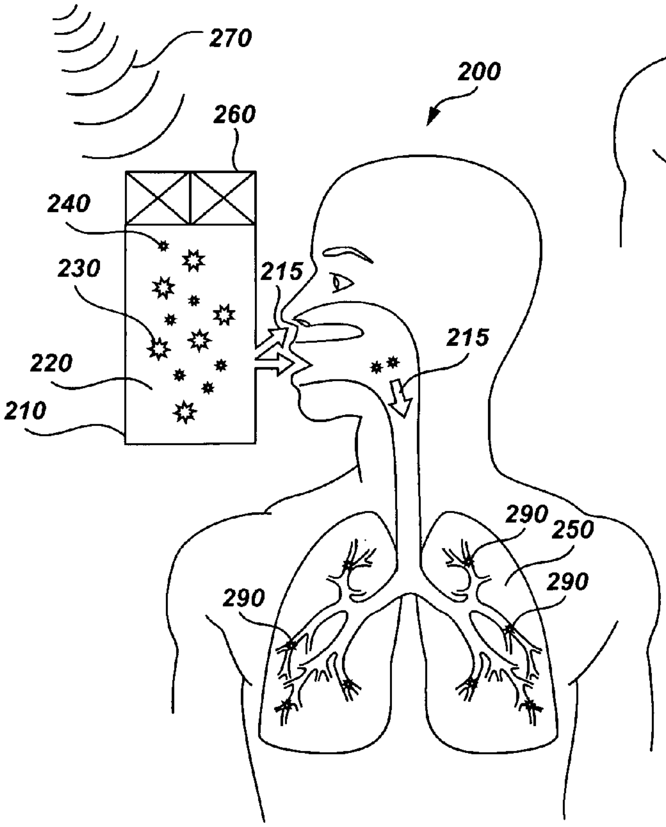

Continuing to refer to FIG. 2, FIG. 2A depicts a partial diagrammatic view of an illustrative embodiment of a method comprising receiving data 260 including data 270 of a physical condition affecting one or more subjects 200, the data 270 informing administration 215 of a pharmaceutical composition 220, 230, 240 in response to the physical condition, wherein the pharmaceutical composition is configured to contact pulmonary tissue 250, 280, 290 to treat a pulmonary disease or condition in the one or more subjects 200. The system or method may include a device 210. The system or method includes providing data 270 including data of a physical condition affecting one or more subjects, the data informing administration 215 of a pharmaceutical composition in response to the physical condition, wherein the pharmaceutical composition 220, 230, 240 contacts pulmonary tissue 250 to treat a pulmonary disease or condition in the one or more subjects. In FIGS. 2B and 2C, the pharmaceutical composition 220 includes at least one agent 230, 240 and is configured to achieve a selected pH range 280, 290 of the pulmonary tissue 250 of the one or more subjects 200. Two or more distinct and non-overlapping particle size ranges 230, 240, may be configured to achieve a selected pH range in the two or more levels, for example, in the bronchus or bronchi 280 of the lungs, or further into the bronchial tree 290 towards the bronchi, bronchioles, alveolar duct, or alveoli of the lungs of the subject.

Figure 3A:
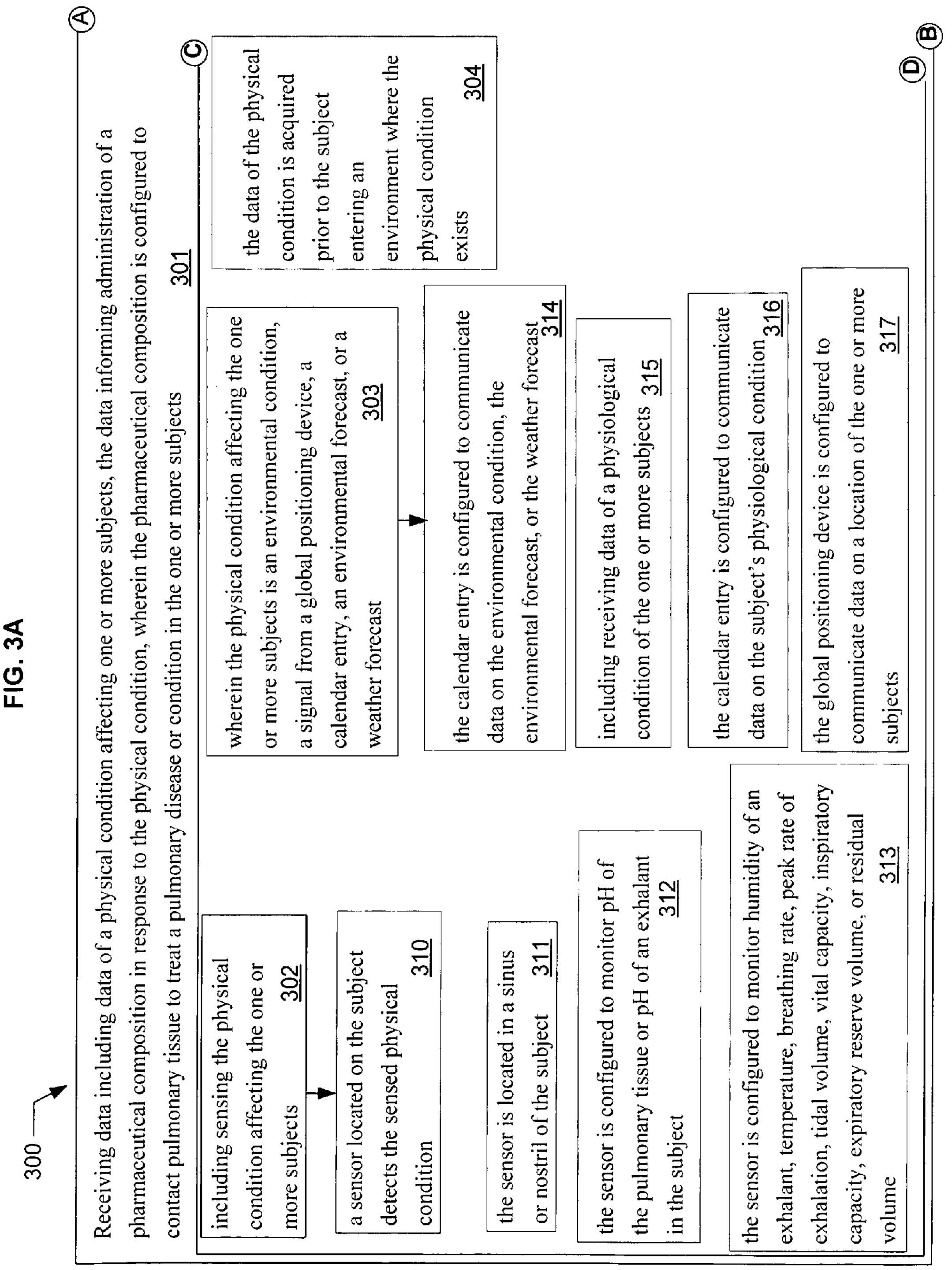
FIGS. 3A and 3B depict a logic flowchart of a method such as those depicted in FIGS. 1 and 2.
Figure 3B:
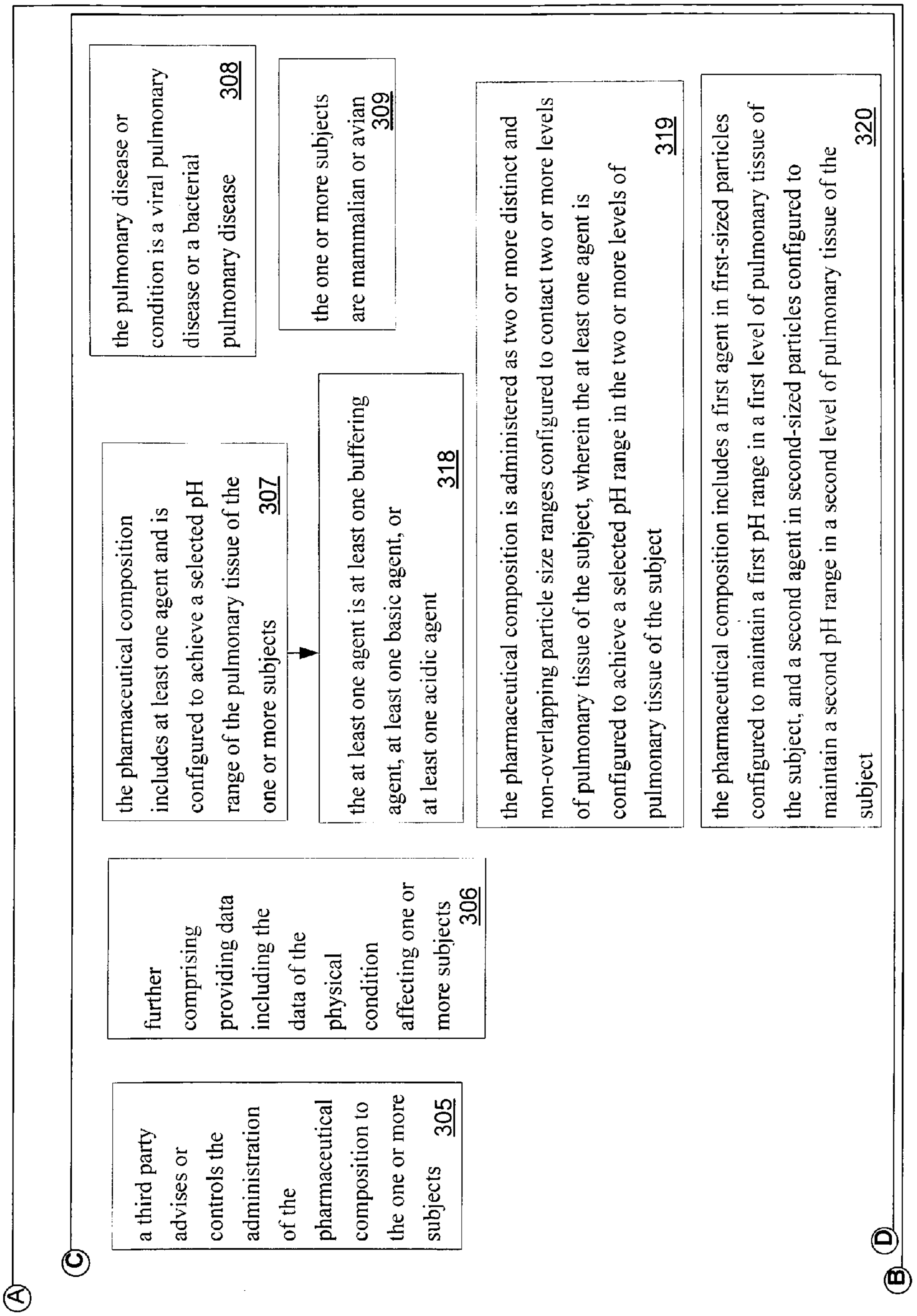

FIGS. 3A and 3B depict a logic flowchart of a method such as those depicted in FIGS. 1 and 2. FIGS. 3A and 3B illustrate an exemplary method 300 for receiving data including data of a physical condition affecting one or more subjects, the data informing administration of a pharmaceutical composition in response to the physical condition, wherein the pharmaceutical composition is configured to contact pulmonary tissue to treat a pulmonary disease or condition in the one or more subjects.

Figure 4:
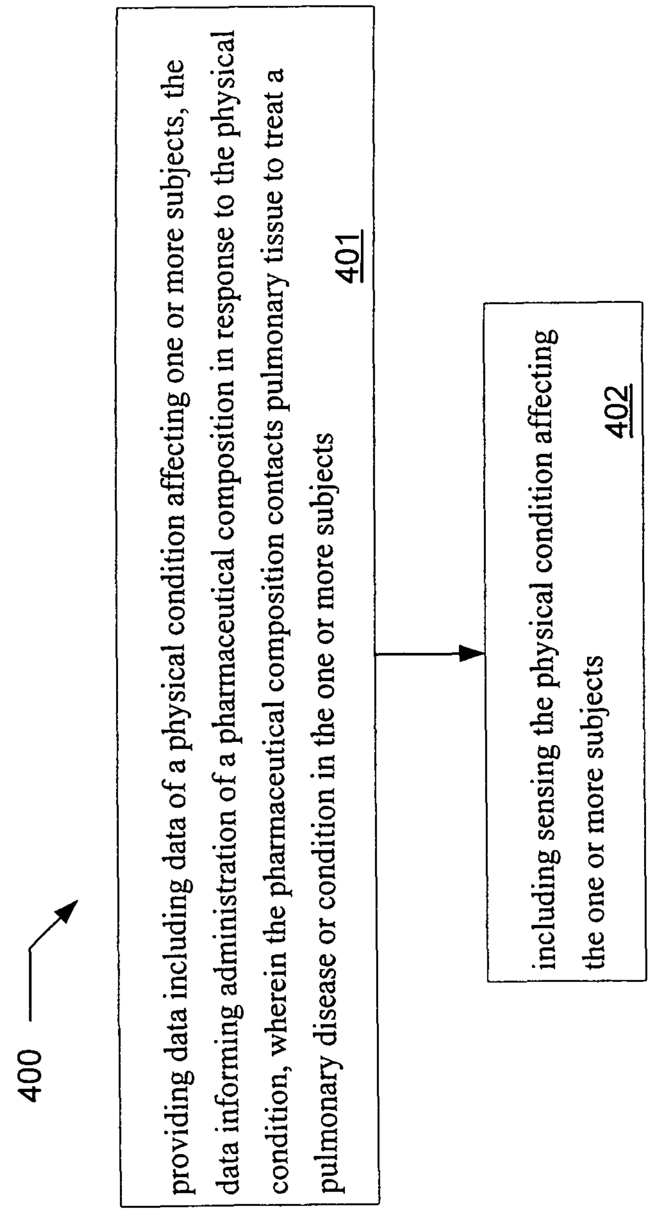
FIG. 4 depicts a logic flowchart of a method such as those depicted in FIGS. 1 and 2.

FIG. 4 depicts a logic flowchart of a method such as those depicted in FIGS. 1 and 2. FIG. 4 illustrates an exemplary method 400 including providing data including data of a physical condition affecting one or more subjects, the data informing administration of a pharmaceutical composition in response to the physical condition, wherein the pharmaceutical composition contacts pulmonary tissue to treat a pulmonary disease or condition in the one or more subjects.

Figure 5:
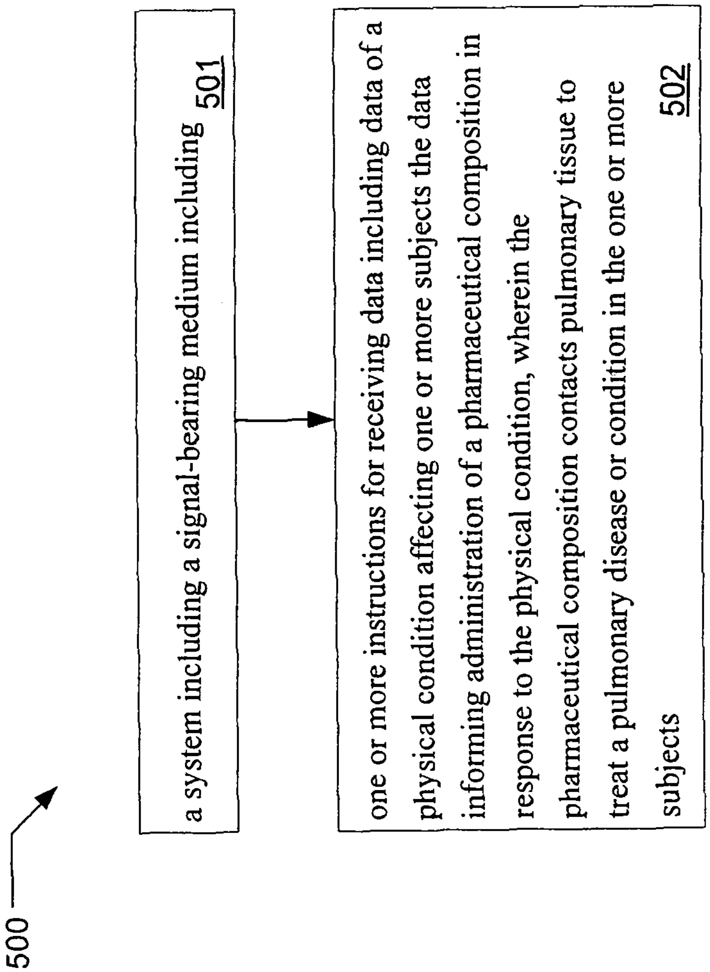
FIG. 5 depicts a logic flowchart of a device such as those depicted in FIGS. 1 and 2.

FIG. 5 depicts a logic flowchart of a device such as those depicted in FIGS. 1 and 2. FIG. 5 illustrates an exemplary device 500 including a signal-bearing medium which includes one or more instructions for receiving data including data of a physical condition affecting one or more subjects the data informing administration of a pharmaceutical composition in response to the physical condition, wherein the pharmaceutical composition contacts pulmonary tissue to treat a pulmonary disease or condition in the one or more subjects.

Figure 6A:
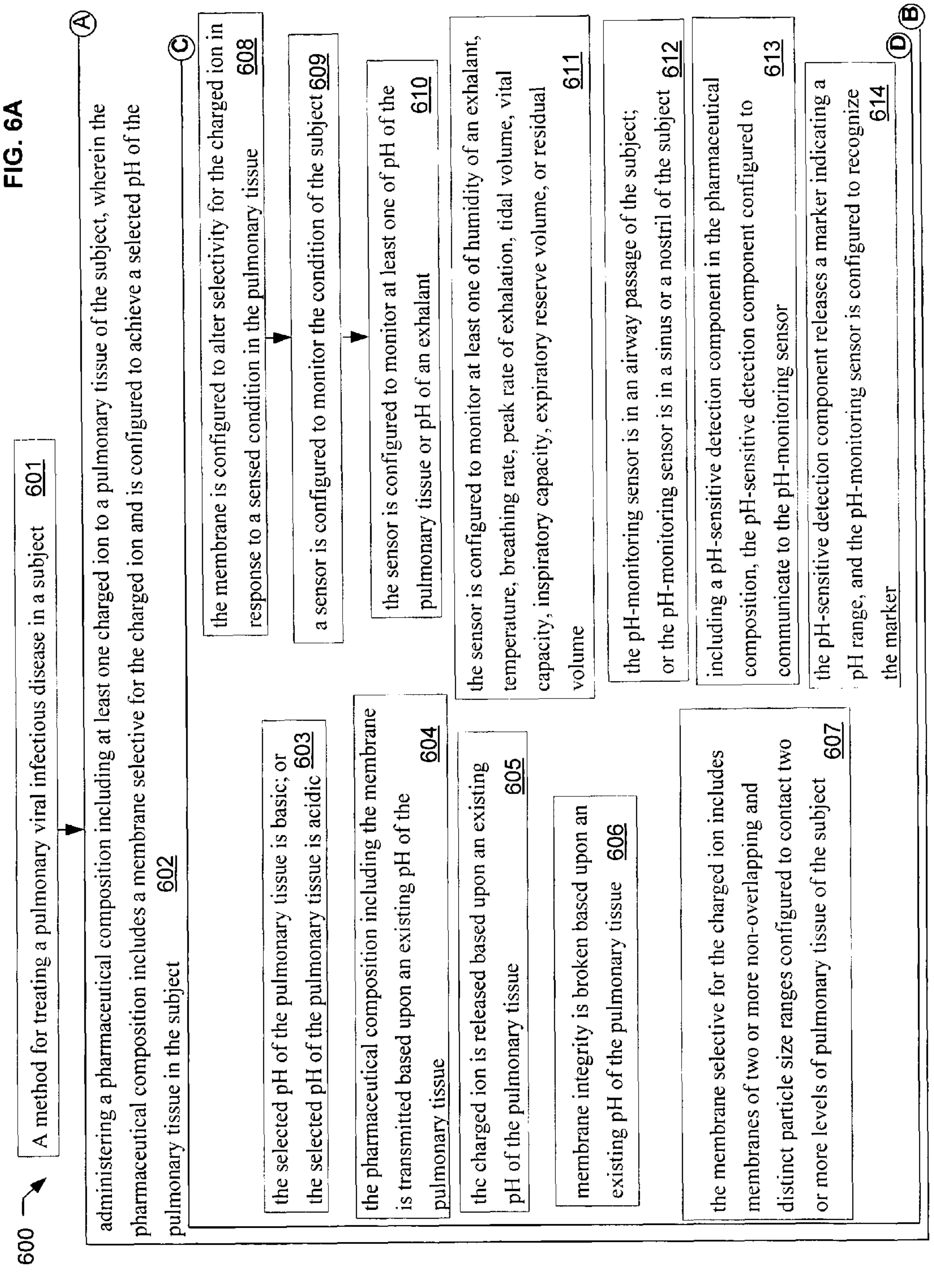
FIGS. 6A, 6B, and 6C depicts a logic flowchart of a method such as those depicted in FIGS. 1 and 2.
Figure 6B:
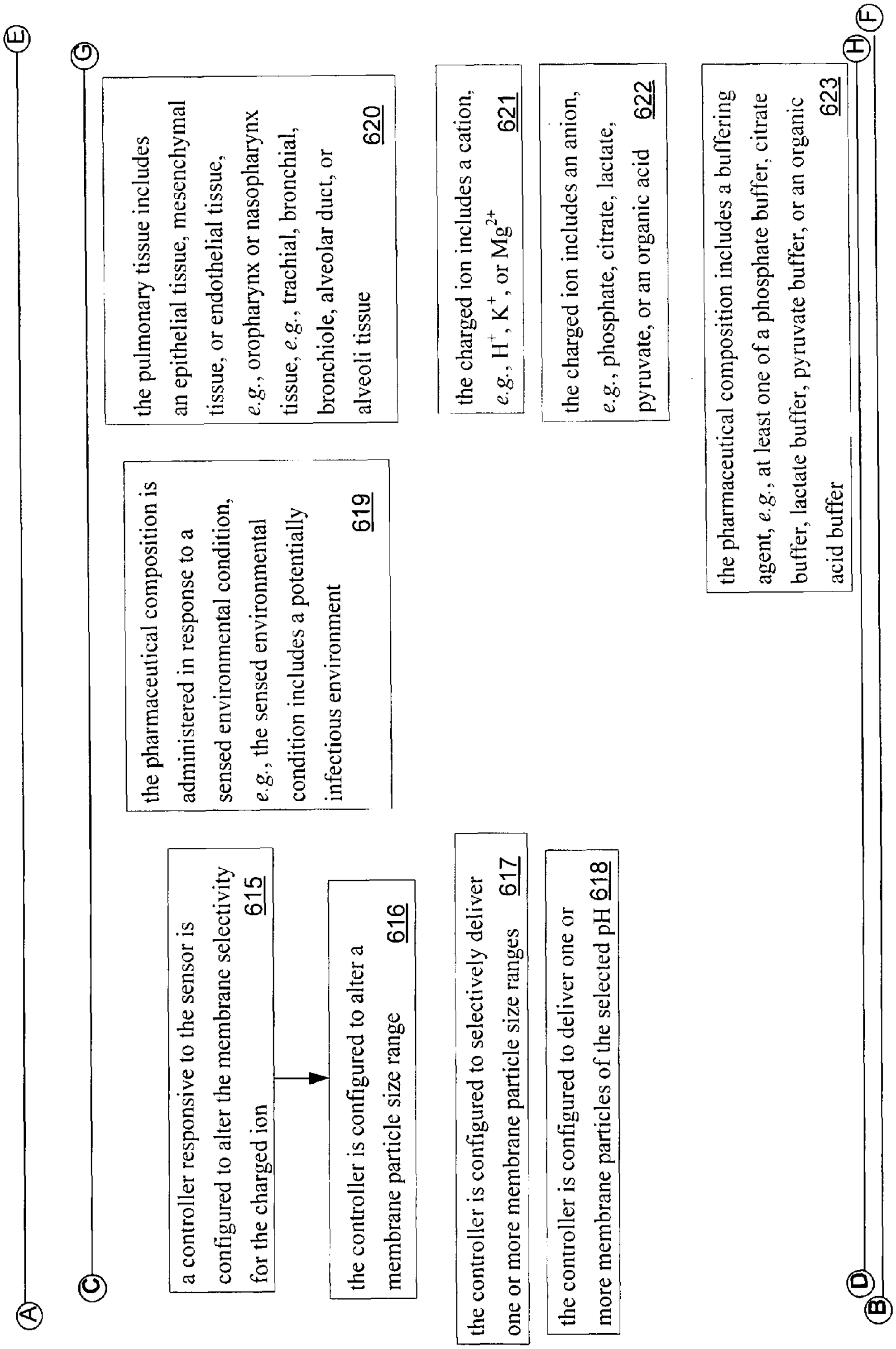
Figure 6C:
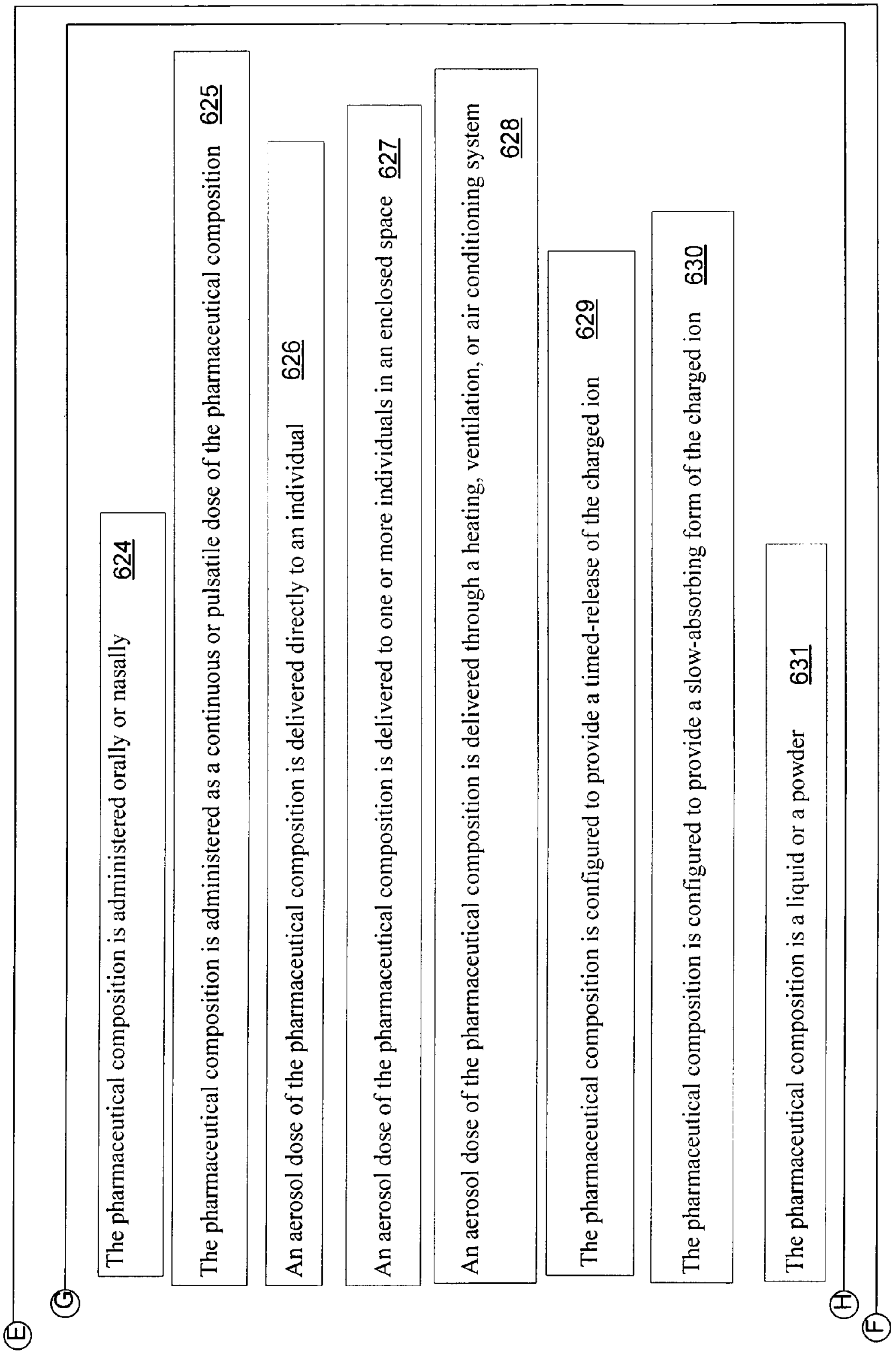

FIGS. 6A, 6B, and 6C depict a logic flowchart of a method such as those depicted in FIGS. 1 and 2. FIGS. 6A, 6B, and 6C illustrate an exemplary method 600 for treating a pulmonary viral infectious disease in a subject which includes administering a pharmaceutical composition including at least one charged ion to a pulmonary tissue of the subject, wherein the pharmaceutical composition includes a membrane selective for the charged ion and is configured to achieve a selected pH of the pulmonary tissue in the subject.

Figure 7:
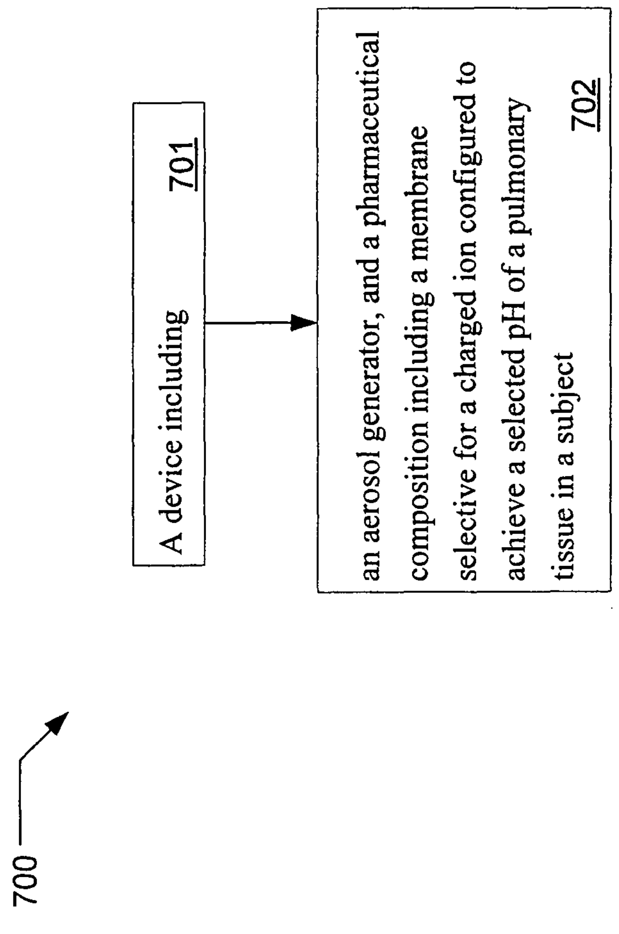
FIG. 7 depicts a logic flowchart of a device such as those depicted in FIGS. 1 and 2.
Figure 8B:
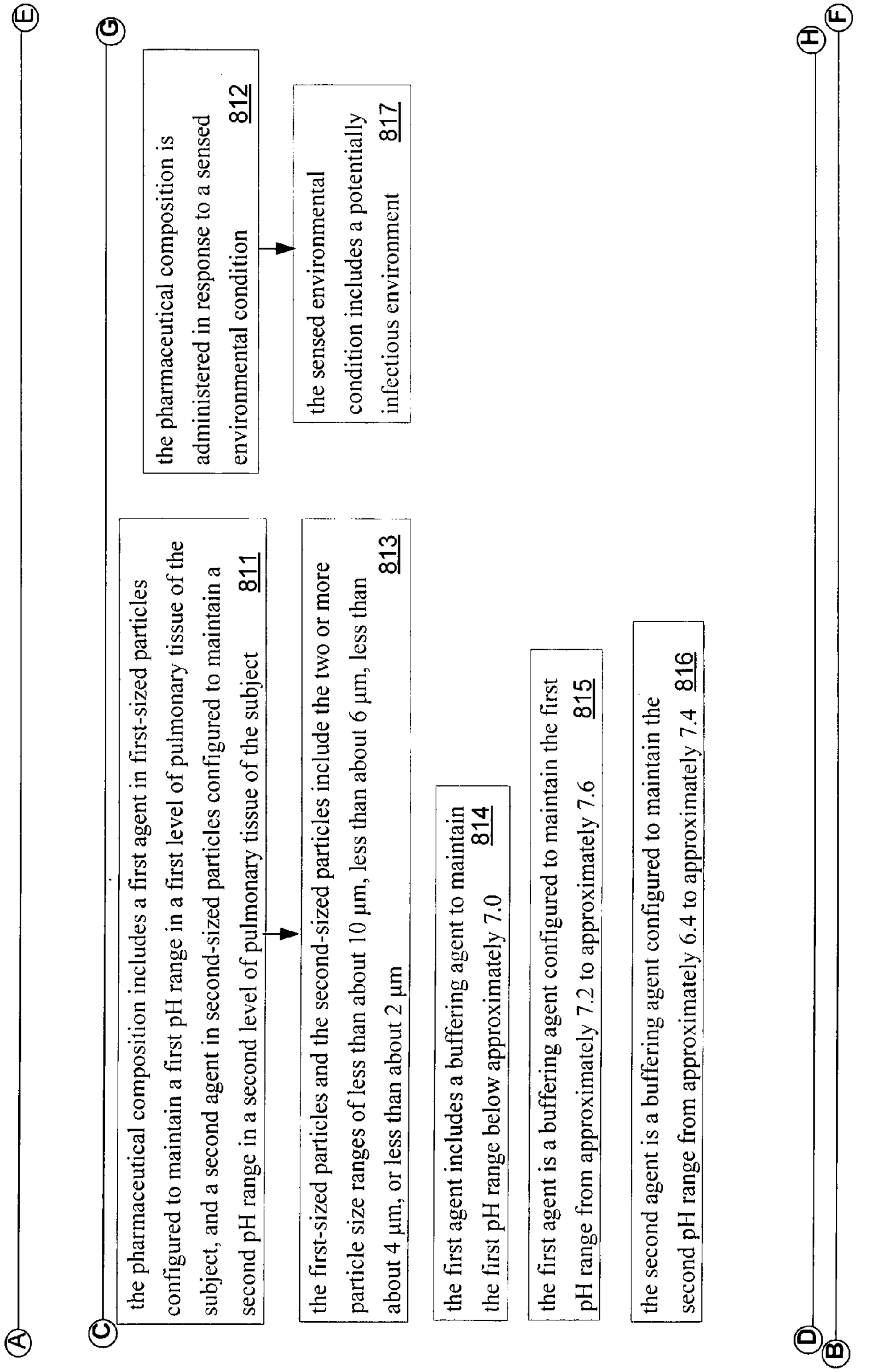
Figure 8C:
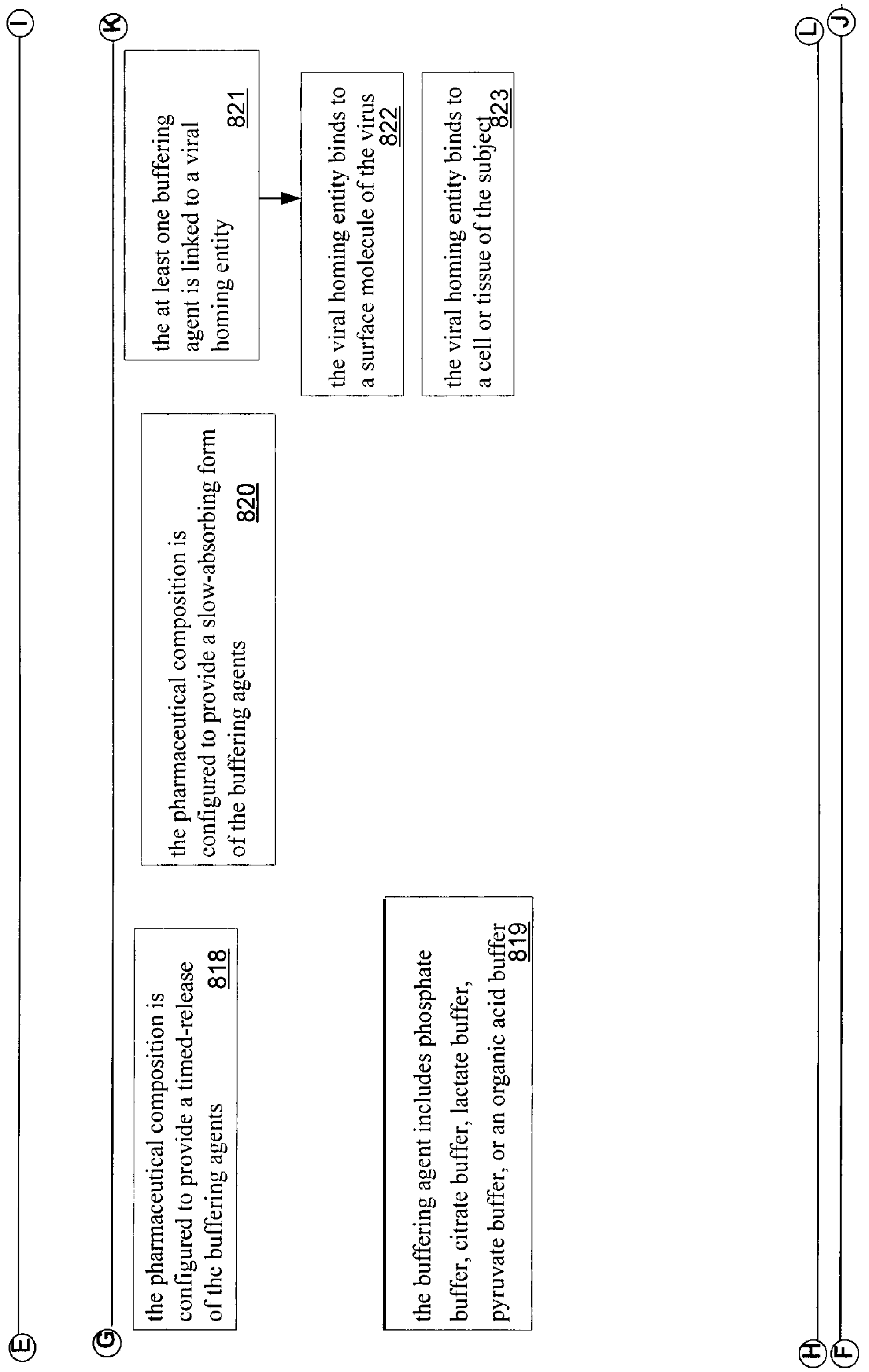
Figure 8D:
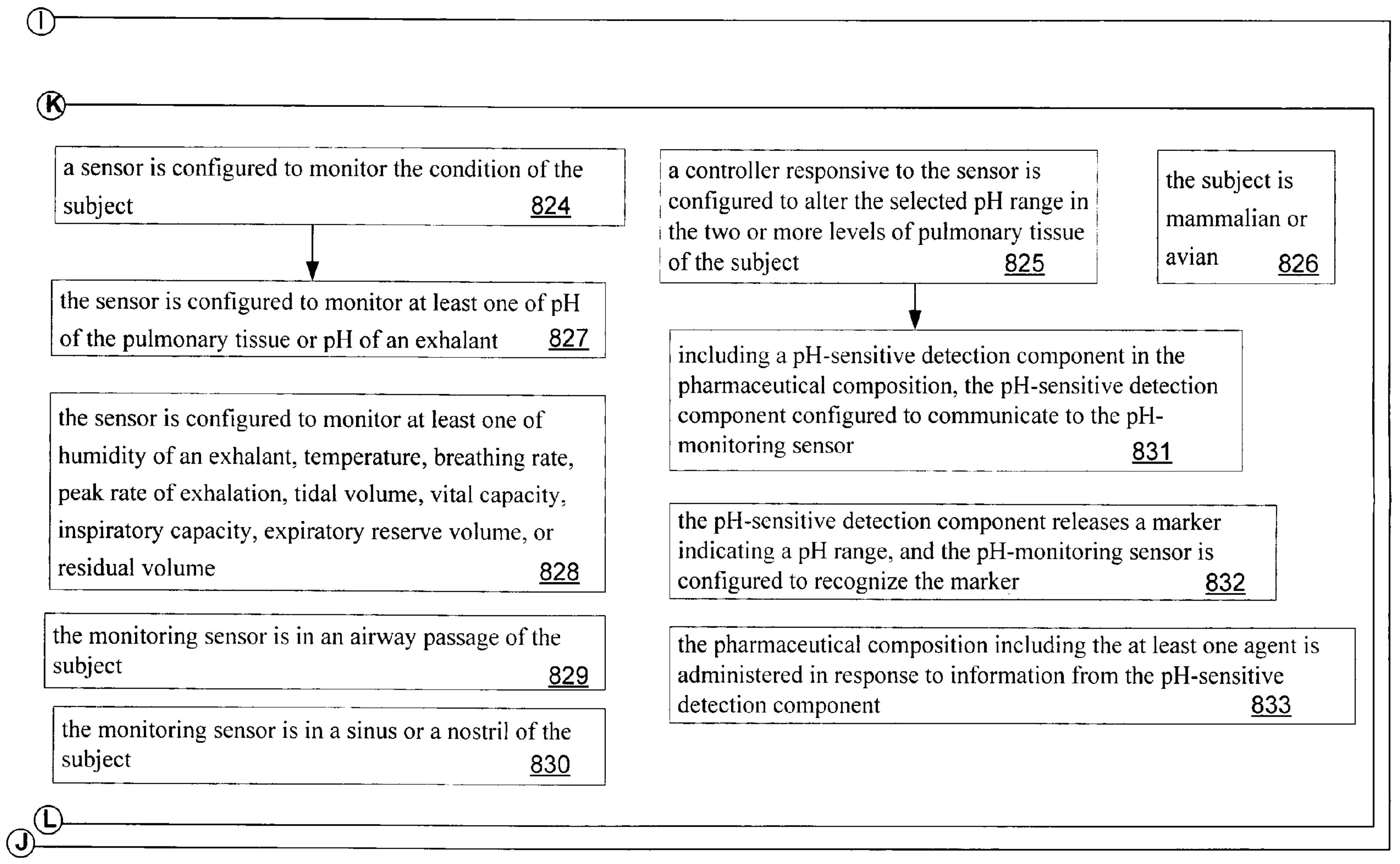

FIG. 7 depicts a logic flowchart of a device such as those depicted in FIGS. 1 and 2. FIG. 7 illustrates an exemplary device 700 including an aerosol generator, and a pharmaceutical composition including a membrane selective for a charged ion configured to achieve a selected pH of a pulmonary tissue in a subject.

FIGS. 8A, 8B, 8C, and 8D depict a logic flowchart of a method such as those depicted in FIGS. 1 and 2. FIGS. 8A, 8B, 8C, and 8D illustrate an exemplary method 800 for treating a pulmonary viral infectious disease in a subject which includes administering a pharmaceutical composition including at least one agent to a pulmonary tissue of the subject, wherein the pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

Effects of Pulmonary pH and Pharmaceutical Composition on Viral Infection in a Subject Methods, compositions, and systems are provided for treating a pulmonary viral infection in a subject wherein administration of a pharmaceutical composition configured to deliver a pH-modifying agent may prevent and/or treat a viral infection. The compositions and methods for treating the pulmonary viral infection may prevent binding, fusion, and replication of the viral particles to pulmonary tissue of the subject. Administration of the pharmaceutical composition may be informed by sensing the pH of the pulmonary tissue of a subject.

The pH within the respiratory system, whether acidic, neutral or basic, may contribute to susceptibility to viral infection in terms of both target cell invasion, replication within the target cell, and release from the target cell. A low pH environment in endocytic and exocytic compartments of a target cell has been shown to be a prerequisite for translocation of a viral particle into the cell cytoplasm. Two examples of viruses that infect the pulmonary tissue and may be influenced by pH include the influenza viruses, associated with flu epidemics, and human rhinoviruses, associated with the common cold. A number of other viruses induce infection within the respiratory system and may be influenced by the pH of the pulmonary tissue. Viruses infectious to the respiratory system include, but are not limited to, parainfluenza virus, coronavirus, respiratory syncytial virus, adenovirus, cytomegalovirus, and hantavirus.

In general, three steps determine the early events in viral infection of a host cell including adsorption to the plasma membrane by binding to specific receptors, penetration, and subsequent uncoating of the genome. Many enveloped and nonenveloped viruses enter a cell via receptor-mediated endocytosis, with membrane penetration and uncoating taking place from the endosomes. Internalization of viral particles is initiated by invagination of the plasma membrane. After pinching off, these vesicles derived from the plasma membrane reach the early endosome compartment. In early endosomes, the internalized material are either are sorted into the recycling pathway or are directed via late endosomes to lysosomes for degradation. Viruses are transported to the compartment providing conditions suitable for delivery to the cytoplasm. The low pH environment, e.g., pH 5.0 to 6.5, in endocytic and exocytic compartments has been shown to be a prerequisite for translocation into the cytoplasm.

Influenza virus is an enveloped negative-sense RNA virus. It is major public health problem worldwide and is responsible for 20,000 deaths annually in the United States alone, with the frequent emergence of new and potentially deadly strains of the virus. As with all viruses, influenza virus needs to penetrate target cells to cause infection. An important component of influenza infectivity is the virally-associated surface glycoprotein hemagglutinin which plays a role in recognition and binding of the virus to host cells as well as fusion of the virus with the host cell membrane. Hemagglutinin consists of a receptor-binding (HA1) domain and a membrane-anchoring (HA2) domain linked by a disulfide bond. Hemagglutinin selectively binds to α-sialosides on glycoproteins and glycolipids associated with the outer surface of the target cells. Different viral hemagglutinins preferentially recognize different sialic acid-galactose linkages. For example, human influenza hemagglutinin preferentially binds alpha 2,6 linkages to galactose while the avian H5N1 influenza hemagglutinin, for example, prefers alpha 2,3 linkages to galactose. The human lung and airway epithelial cells, a prime target for influenza infection, have an abundance of alpha 2,6 linkages. The ability of hemagglutinin to bind to sialylated cell surface receptors may be pH dependent.

The influenza viral particles bound to the target cells through the interaction of hemagglutinin with sialylated cell surface receptors are taken up by the target cell through the process of endocytosis. The low pH environment of the endosomes induces a large conformational change in hemagglutinin which in turn is thought to trigger fusion between the viral and the endosomal membranes. The optimal pH range for membrane fusion by hemagglutinin is between 5 and 5.5. The low pH environment of the endosome also activates the influenza virus M2 protein ion channel which begins to conduct protons across the viral membrane. The lowered internal virion pH is though to weaken protein-protein interactions between the viral matrix protein (M1) and the ribonucleoprotein (RNP) core. Preventing the release of M1 protein results in incomplete viral uncoating and attenuated viral replication (see, e.g., Takeda et al., *J. Virol.* 76:1391-1399, 2002, which is incorporated herein by reference). As such, modulating the pH within the pulmonary tissue may influence influenza infectivity (see, e.g., U.S. Patent Application 2008/0000473 A1, which is incorporated herein by reference).

In some instances, lowering the pH of the pulmonary tissue with one or more acidic agents may prevent hemagglutinin and consequently the influenza virus from binding to the target cells in the first place. It is conceivable that premature exposure of virus to low pH in the extracellular environment might induce conformational changes to glycoproteins spike on the virus surface, thereby interfering with initial binding to the target host cell (see, e.g., Rennie, et al., *Respir. Res.* 8:38, 2007, which is incorporated herein by reference).

Human rhinoviruses, the most frequent cause of upper respiratory tract infections known as “the common cold”, may be inactivated by acidic solutions at or below pH 5.3 (see, e.g., Kurht, et al., *Antimicrob. Agents Chemother.* 26:924-927, which is incorporated herein by reference). Inactivation of rhinoviruses by low pH is thought to be due to conformational changes in capsid proteins at pH values of less than 6.2, leading to loss of the VP4 subunit of the capsid and rendering the virus noninfectious. Treatment of mammalian cells infected with rhinovirus with acidic solutions such as, for example, citrate/phosphate buffer (pH 5.0), ascorbate (pH 5.0), or phthalate (pH 5.0), reduce viral titer by as much as 90% (see, e.g., Gem, et al., *J. Infect. Dis.* 195:1137-1143, 2007, which is incorporated herein by reference).

Influenza viruses may also be inactivated by low pH. For example, Influenza A Sydney/5/95 [H3N2], Influenza A Hong Kong/8/68 [H3N2] and avian reassortment virus A/Washington/897/80 X A Mallard/New York/6750/78 [H3N2] are rapidly inactivated in vitro by contact with acid buffered solutions at pH 3.5 (see, e.g., Rennie et al., *Respir. Res.* 8:38, 2007, which is incorporated herein by reference.

As such, modifying the pH of the pulmonary tissue with a pharmaceutical composition configured to deliver a pH modifying agent may prevent and/or treat a viral infection by preventing binding, fusion, and replication of the viral particles. Administration of the pharmaceutical composition may be informed by sensing the pH of the pulmonary tissue of a subject.

Methods, Compositions, and Systems for Sensing pH of a Pulmonary Tissue in a Subject The methods, compositions, and systems may include a sensor configured to monitor a condition of a subject, e.g., at least one of pH of the pulmonary tissue or pH of an exhalant of a subject. In further aspects, the sensor may be configured to monitor at least one of humidity of an exhalant, temperature, breathing rate, peak rate of exhalation, tidal volume, vital capacity, inspiratory capacity, expiratory reserve volume, or residual volume in the subject. The sensor may be part of a device, such as a hand held device. Alternatively, the sensor may be associated with a mask warn over the mouth and or nose of the subject. In some instances, the sensor may be miniaturized and temporarily or permanently incorporated into an airway passage of the subject. The sensor sends the data regarding the pH of the pulmonary tissue/exhalant of a subject to a second component of the device that may automatically administer a pharmaceutical composition to a subject. In one aspect the second component is a controller. The controller may be responsive to the sensor and configured to alter the membrane selectivity for the charged ion. Alternatively, the sensor sends the data to the subject and/or to a third party caregiver, for example, whereupon the subject and/or third party caregiver may choose to administer a pharmaceutical composition or to alter the dosage of the pharmaceutical composition.

The pulmonary pH of a subject may be monitored in the expired breath of the subject. For example, pH may be monitored in expired breath condensate (EBC). EBC consists of: (1) aerosolized particles of airway lining fluid evolved from the airway wall by turbulent airflow, that serves as seeds for substantial; and (2) water vapor condensation, which then serves to trap (3) water soluble volatile gases. The normal range of pH values of fluid lining human airways ranges from pH 6.5 to pH 7.5 (see, e.g., Tanaka, et al., *Eur. Respir. J.* 11:1301-1306, 1998, which is incorporated herein by reference). Sampling may be accomplished by having a subject breath at tidal volumes orally into a mouthpiece attached to a cold condenser (RTube, Respiratory Research Inc., Austin, Tex.; ECoScreen II, VIASYS Healthcare, Yorba Linda, Calif.). In this instance, pH may be assayed after. Argon deaeration of the EBC. In addition to oral collection methods, EBC may be collected through a nasal cannula and or an endotracheal tube. Collection times may be as short as 90 seconds or over an hour to obtain sufficient EBC. Ten minutes of breathing is commonly employed. Alternatively, pulmonary pH of a subject may be monitored in real time using a miniaturized self-condensing pH sensor as described by Tsukashima, et al., in U.S. Patent Application 2007/0068810 A1, which is incorporated herein by reference.

In some instances, the pH of expired breath condensate (EBC) may be monitored by a micro-sensor using a pH sensitive ion-sensitive effect transistor (ISFET). In this instance, a metal oxide such as $SiO_2$, $Ta_2O_5$, and or $Al_2O_3$, for example, may donate or accept a proton from the solution (in this instance the breath condensate) and leave a negatively charged or a positively charged surface group, respectively, thus generating a surface potential that varies depending upon the pH of the solution (see, e.g., U.S. Pat. Nos. 6,132,893 and 6,464,940, which are incorporated herein by reference).

The sensor as provided in the method, composition, or system for monitoring the pH in the expired breath condensate of the subject may be sufficiently small to be semi-permanently or permanently located in a segment of the airway of a subject. The sensor may be incorporated into the upper respiratory tract, including, but not limited to, the nasal cavity, pharynx and or larynx. Alternatively, the sensor may be incorporated into a dental or nasal prosthesis (see, e.g., U.S. Patent Application 2007/0106138 A1, which is incorporated herein by reference) or into a piece of jewelry such as, for example, a nose or tongue piercing (see, e.g., U.S. Patent Application 2005/0209526 A1, which is incorporated herein by reference).

Alternatively, the sensor for monitoring the pH in the expired breath condensate of the subject may be incorporated into a mask or other covering of the mouth and/or nose that is worn by the subject (see, e.g., U.S. Patent Application 2007/0068810 A1, which is incorporated herein by reference). In some instances, the mask may be worn at all times, and as such may continuously and in real time measure the pH of the expired breath condensate of a subject. Alternatively, the mask may be worn temporarily to measure the pH of the expired breath condensate of a subject at any given point in time.

The method, composition, or system as provided herein may further include a sensor configured to monitor other physiological conditions of a subject such as, pH of the pulmonary tissue or pH of an exhalant of a subject. The sensor may be configured to monitor further conditions which include, but are not limited to, humidity of an exhalant, temperature, breathing rate, peak rate of exhalation, tidal volume, vital capacity, inspiratory capacity, expiratory reserve volume, or residual volume.

Sensing a Potentially Infectious Environment

In some aspects, data regarding an environmental condition is sensed by a subject or projected or forecast to be sensed by a subject and may be sent to and received by the device or measured by the method, composition, or system. The data regarding an environmental condition either alone or in combination with data regarding the pH of the pulmonary tissue of a subject may further inform the administration of a pharmaceutical composition to prevent or treat an infectious condition in the subject. An environmental condition may include, for example, a potentially infectious environment.

The condition of a potentially infectious environment may be directly measured by assessing the presence or absence of airborne pathogens. Airborne pathogens such as viral particles, for example, may be detected by recovering the particles in or on a collection medium (e.g., liquid, semisolid, or solid substrate), and then assaying the substrate for the presence of the targeted virus using an appropriate assay system. In one aspect, airborne viral articles may be collected using an impinger in which a converged stream of environmental air is directed onto a liquid collection medium (see, e.g., Hermann, et al., *Appl. Environ. Microbiol.* 72: 4811-4818, 2006, which is incorporated herein by reference). Other capture mediums include, but are not limited to filters, bubblers, or impactors. Real time polymerase chain reaction (RT-PCR) amplification may be used to detect and identify viral pathogens. For example, Chen, et al., describe methods for using RT-PCR to detect and identify the avian H5N1 influenza virus (Chen et al., *J. Med. Microbiol.* 56: 603-607, 2007, which is incorporated herein by reference). Similarly, airborne rhinovirus may be collected on Teflon membranes and identified and quantified by PCR (see, e.g., Myatt, et al., BMC Public Health 3:5, 2003, which is incorporated herein by reference). Alternatively, airborne pathogens may be detected using some form of microsensor. In one aspect, arrays of silicon cantilever beams may be used as microresonator sensors to detect individual virus particles (see, e.g., Gupta, et al., *Applied Physics Lett.* 84: 1976-1978, 2003, which is incorporated herein by reference).

Alternatively, the condition of a potentially infectious environment may be implied from the time of year and global location. For example, "flu" season or that portion of the year in which there are regular outbreaks of influenza infections usually occurs in the cold half of the year in each hemisphere. In the United States, for example, flu season may run from November through March of the following year. During the colder portion of the year, people remain indoors more often and as such brings people into closer contact, allowing for easier viral transmission. In addition, cold temperatures lead to drier air and may dehydrate mucus and thus prevent the body from effectively expelling virus particles. The virus itself may survive longer on surfaces in cold temperatures.

The condition of a potentially infectious environment may be communicated to a subject or group of subjects from an agency tracking viral infection in a given location. Such an agency might be, for example, a local Public Health authority, the Center for Disease Control (CDC), the World Health Organization (WHO) or similar agencies in a given location. The location may be the current location of a subject. Alternatively, the location may be the location to which the subject will be traveling to in the near future. The CDC provides weekly influenza surveillance data broken down by region such as Northeast versus Pacific.

During the "flu" season, exposure to potentially infected individuals in enclosed and crowded spaces such as, for example, buses, trains, airplanes, elevators, schools, childcare, medical facility, and others, may increase the risk of contracting a viral infection. As such, the method or device may further include a global positioning system as well as a calendar of scheduled activities of a subject to predict and monitor when a subject has or will be entering a potentially infectious environment. Upon receiving data regarding the potentially infectious environment, the device may automatically administer the pharmaceutical composition including at least one agent to a pulmonary tissue of the subject. Alternatively, the device may communicate the data to the subject who may than choose to self-administer the pharmaceutical composition.

The method, composition, or system may further receive data or sense data regarding other environmental conditions that may contribute to increased susceptibility to viral infection. Other environmental conditions that may contribute to increased susceptibility to viral infection include, but are not limited to, poor air quality associated with smog, forest fire, volcanic ash; allergen conditions such as pollen count, mold spores, dander; and weather conditions such as temperature, pressure, wind speed and humidity.

Therapeutic Pharmaceutical Compositions and Formulations

Methods, compositions, and systems are provided wherein the pharmaceutical composition may be one or more agents that may be used to adjust the pH within the pulmonary tract of the subject. The pharmaceutical composition may include at least one agent to a pulmonary tissue of the subject, wherein the pharmaceutical composition is administered as two or more distinct and non-overlapping particle size ranges configured to contact two or more levels of pulmonary tissue of the subject. The one or more pharmaceutical agents may be one or more of a basic agent, an acidic agent, a buffering agent, or some combination thereof. The pharmaceutical composition may be one or more basic agent comprising a proton acceptor for raising the pH in the airways such as, for example, ammonia or bicarbonate. Alternatively, the pharmaceutical composition may be one or more acidic agent comprising a proton donor for lowering the pH in the airways such as, for example, acetic acid, ascorbic acid, citric acid, phytic acid, succinic acid, glutaric acid, phosphoric acid, or dilute hydrochloric acid, or other proton donors. The pharmaceutical composition may be one or more buffering agents, including, but not limited to, sodium bicarbonate, potassium bicarbonate, phosphate buffer, citrate buffer, lactate buffer, pyruvate buffer, phthalate buffer, glycine (amino acetic acid), bicine (N,N-bis(2-hydroxyethyl)glycine), tricine (N-[tris(hydroxymethyl)methyl]glycine), CAPS (3-(cyclohexamino)-1-propanesulphonic acid, CAPSO (3-(cyclohexamino)-2-hydroxypropanesulphonic acid), 2-(cyclohexamino)-ethenesulphonic acid, BIS-TRIS propane, MOPS, HEPES, DIPSO, TAPSO, TRIZMA, HEPPSO, POPSO, EPPS, dibasic sodium phosphate, dibasic potassium phosphate, or triethanolamine.

In some instances, the pharmaceutical composition may include one or more agents used for treating a viral infection. Examples of agents used for treating influenza, for example, include, but are not limited, to neuraminidase antagonists as exemplified by zanamivir and oseltamivir and M2 viral channel antagonists as exemplified by amantadine and rimantadine. Other antiviral drugs of the pharmaceutical composition may include, but are not limited to acyclovir, valacyclovir, famciclovir, penciclovir, trifluridine, ganciclovir, valganciclovir, cidofovir, abacavir, didanosine, emtricitabine, lamivudine, stavudine, tenofovir, zalcitabine, zidovudine, delavirdine, efavirenz, nevirapine, atazanavir, darunavir, fosamprenavir, indinavir, lopinavir, nelfinavir, ritonavir, saquinavir, tipranavir, interferon alfa, adefovir dipivoxil, entecavir, and ribavirin.

In some instances, the pharmaceutical composition may include one or more agents used for treating the symptoms of a viral or bacterial infection or treating in response to an allergen. The pharmaceutical composition may include one or more decongestants, including, but are not limited, oxymetazoline, phenylephrine, xylometazoline, or pseudoephedrine. The pharmaceutical composition may also include an expectorant, e.g., guaifenesin. The pharmaceutical composition may further include an antihistamine, including, but are not limited, carbinoxamine, dimenhydrinate, diphenhydramine, tripelennamine, hydroxyzine, cyclizine, meclizine, brompheniramine, chlorpheniramine, promethazine, cyprohetadine, fexofenadine, loratadine, or cetirizine. Formulating a pharmaceutical composition as a dry powder for inhalation may involve either micronization via jet milling, precipitation, freeze-drying or spray-drying using various excipients, such as lipids and polymers, or carrier systems such as lactose.

Pharmaceutical Composition and Particle Size

In some aspects of the methods, compositions, and systems provided herein, it may be beneficial to alter the pH, e.g., lower or raise the pH, in one level of the pulmonary tree while maintaining the pH in another level of the pulmonary tissue. Directing the pharmaceutical composition to one or more levels of the pulmonary tissue may be accomplished by varying the particle size of the one or more agents of the pharmaceutical composition. This may be dictated by where in the pulmonary tissue a particular viral infection is likely to occur. For example, human rhinoviruses commonly infect epithelial cells in the upper respiratory tract (see, e.g., Whiteman, et al., *J. Biol. Chem.* 278:11954-11961, 2003, which is incorporated herein by reference). As such, the pharmaceutical composition may be directed specifically to the upper respiratory tract, for example, for the prevention and treatment of human rhinoviruses. In some instances, similar viral strains may target host cells in different locations within the respiratory tract (see, e.g., (see, e.g., Uiprasertkul, et al., *Emerging Infectious Dis.* 11:1036-1041, 2005; Matrosovich, et al., *PNAS* 101: 4620-4624, 2004, which are incorporated herein by reference). For example, human influenza A specifically targets epithelial cells in the upper respiratory tract that express the 2,6-linked sialyl-galactosyl moieties. In contrast, avian influenza (H5N1) targets epithelial cells expressing the 2,3-linked sialyl-galactosyl moieties. These cells in humans are primarily located deep in the lower respiratory tract in ciliated epithelial cells and Type II pneumocytes. The pharmaceutical composition may be selectively directed to a level or levels of the pulmonary tissue based on the potential viral infection site, the latter of which is dependent upon which virus a subject has been exposed to or may be exposed to in the future. Directing the pharmaceutical composition to one or more levels of the pulmonary tissue may be accomplished by varying the particle size of the one or more agents of the pharmaceutical composition.

The pharmaceutical composition may be administered as two or more particles sizes of the same or different pH modifying agent for delivery to different levels of the pulmonary tissue. The two or more particle sizes may range from approximately 1 to 4 μm, approximately 5 to 10 μm, approximately 15 to 40 μm, or approximately 50 to 100 μm. The two or more particle sizes may range from approximately less than about 10 μm, less than about 6 μm, less than about 4 μm, less than about 2 μm, or less than about 1 μm. The particle size of a pharmaceutical composition is an important variable in defining the dose deposited and the distribution of the pharmaceutical composition in the pulmonary tissue (see, e.g., Labiris & Dolovich, *Br. J. Clin. Pharmacol.* 56:588-599, 2003, which is incorporated herein by reference). Fine particles more readily distribute in the peripheral airways while larger particles may deposit in the central airways or upper respiratory tract. A particle size may be defined by its mass median aerodynamic diameter (MMAD). Particles may be deposited by inertial impaction, gravitational sedimentation or diffusion depending upon their size. While deposition occurs throughout the airways, inertial impaction generally occurs in the first 10 generations of the lung where the air velocity is high and flow is turbulent. Deposition by gravitational sedimentation predominates in the last five to six generations of the airways (smaller bronchi and bronchioles) where air velocity is low. In the alveoli region, air velocity is negligible and as such particles are deposited by sedimentation and diffusion. Those particles not deposited during inhalation are exhaled.

In general, larger particles do not readily follow changes in air flow direction and tend to deposit by inertial impaction in the upper respiratory tract. For example, most particles greater than 10 μm are deposited in the oropharyngeal region with a large amount impacting on the larynx. Aerosols with MMAD of 5-10 μm are mainly deposited in the large conducting airways as well as in the oropharyngeal region. Intermediate sized particles (3-5 μm) are carried farther into the small airways of the bronchi and bronchioles, with 50% of 3 μm particles reaching the alveolar region. Particles that are less than 3 μm may behave more like gas molecules following the airflow all the way to the alveoli. However, very small particles of less the 0.5 μm, for example, may fail to be deposited in the alveoli and instead may be exhaled.

Deposition of a pharmaceutical composition in the lungs may also be controlled by the inspiratory flow rate, the tidal volume and respiratory frequency of the subject (see, e.g., Labiris & Dolovich, *Br. J. Clin. Pharmacol.* 56:600-612, 2003, which is incorporated herein by reference). Controlling the air velocity or inspiratory flow rate by slow inhalation will maximize the number of particles that reach the alveoli and minimize the number that are exhaled. For example, fast inhalations may result in reduced peripheral deposition because the aerosol is more readily deposited by inertial impaction in the conducting airway and oropharyngeal region. When aerosols are inhaled slowly, deposition by gravitational sedimentation in peripheral region is enhanced. Peripheral deposition may also be increased with an increased in tidal volume and a decrease in respiratory frequency. As such, holding one's breath after inhalation may enable better penetration of composition into periphery of lungs.

The particle size and deposition depth of the pharmaceutical composition entering the lungs is a function of the inhaler device used and the formulation of the pharmaceutical composition. Inhalers and nebulizers of different types each have the ability to generate aerosol particles of a certain size range. For liquid formulations containing soluble pharmaceutical compositions, the size of the aerosol particle is largely a function of the design and operation of the delivery device such as the nebulizer or "atomizer" that converts the liquid into a vapor or mist. For pharmaceutical compositions in powder form and for insoluble pharmaceutical compositions that are suspended or dispersed in emulsions, the particle size in the formulation of the pharmaceutical composition is an important determining factor.

The particle size and deposition depth of the pharmaceutical composition entering the lungs is a function of the formulation of the pharmaceutical composition. Ideally the formulation retains the activity of the pharmaceutical composition as well as efficiently delivers the composition to the appropriate site of action within the lungs and allows the composition to remain in the lungs long enough to have the desired pharmacological effect. Formulating a pharmaceutical composition as a dry powder for inhalation may involve, e.g., either micronization via jet milling, precipitation, freeze-drying or spray-drying using various excipients, such as lipids and polymers, or carrier systems, such as lactose or other sugars. Particles of different sizes may be generated by modifications to the methods described above.

The size of one or more particles of the pharmaceutical composition may be measured using any of an number of methods including, but not limited to, light scattering, x-ray sedimentation, electrical sensing using the Coulter principle, sieves, spectroscopy, and microscopy combined with image analysis. In one aspect, microscopy, e.g., optical microscopy, scanning electron microscopy, laser scanning microscopy, confocal microscopy or scanning probe microscopy may be combined with image analysis software to determine the size and shape of particles (see, e.g., U.S. Pat. No. 7,009,169, which is incorporated herein by reference). The Clemex Particle Size Analyzer—PS3 is an example of a commercially available instrument for measuring particle size and shape using microscopy and image analysis (from Clemex Technologies, Inc., Longueuil, Canada). Another common method for particle size determination is to use a light scattering instrument which measures the average particle size of a population of particles as well as the distribution of the particle size of the particles. When light strikes a particle, scattering (diffraction) occurs. The light scatters in all directions, but for larger particles there is relatively more scattering to the front while for smaller particles there is relatively more scattering to the sides and back. The light scattering method reports a three-dimensional (i.e., volume) equivalent sphere diameter. One example of a commonly used light scattering instrument is the Horiba LA-920 laser light diffraction instrument (from Horiba Instruments, Inc., Irvine, Calif.). The light scattering method is particularly adapted to measuring particle size and particle size distributions of the small particles in a dispersion.

One or more particles may be sized to generate a monodisperse population of particles. Particles that are dry powder polydisperse powder particles, for example, may be sized using a series of individual and or nested sieves that may further contain beads, disks and/or other non-geometric shapes that are rotated, vibrated or agitation in any of a number of directions to generate monodisperse particles (see, e.g., U.S. Pat. No. 6,267,310, and U.S. Pat. No. 6,197,835 which are incorporated herein by reference). The monodisperse population may be characterized using the particle size analysis methods described above.

Pharmaceutical Composition with pH Sensitive Marker

The at least one pharmaceutical composition as provided herein administered to a subject may include one or more pH-sensitive detection component configured to communicate with a pH-monitoring sensor. The pH-sensitive detection component releases a marker indicating a pH range, and the pH-monitoring sensor is configured to recognize the marker. The pharmaceutical composition including the at least one agent is administered in response to information from the pH-sensitive detection component.

The pH sensitive detection component of the pharmaceutical composition may be a pH sensitive dye that changes properties in response to pH. Examples of dyes that change color in a pH range compatible with physiological pH levels include, but are not limited to alizarin sulphonic acid (pH 4.3 to 6.3; yellow to violet), methyl red (pH 4.4 to 6.2; red to yellow/orange), chlorophenol red (pH 4.8 to 6.4; yellow to purple), litmus (pH 5.0 to 8.0; red to blue), bromocresol purple (pH 5.2 to 6.8; yellow to purple), bromophenol red (pH 5.2 to 6.8; orange/yellow to purple), 4-nitrophenol (pH 5.4 to 7.5; colorless to yellow), bromoxylenol blue (pH 5.7 to 7.5; yellow to blue), bromothymol blue (pH 6.0 to 7.6; yellow to blue).

Alternatively, the pH sensitive detection component of the pharmaceutical composition may be a pH sensitive fluorescent dye. For example, the pH sensitive detection component may be a pH sensitive fluorescent dye such as LysoSensor Yellow/Blue DND-160 (Invitrogen Inc., Carlsbad, Calif.) which undergoes a pH dependent emission and excitation shift to longer wavelengths in acidic environments. Examples of pH sensitive dyes include, but are not limited to, other LysoSensor probes, e.g., LysoSensor Blue DND-167 and LysoSensor Green DND-189 which are almost nonfluorescent except when inside acidic compartments; and fluorescein containing dyes such as dichlorofluorescein, carboxydichlorofluorescein, carboxydifluorofluorescein, and BCECF; and Oregon Green 514 carboxylic acid, Oregon Green 488 carboxylic acid, 5-(and 6-)carboxy-2',7'-, 9-amino-6-chloro-2-methoxyacridine (ACMA) (e.g., Invitrogen Inc., Carlsbad, Calif.).

Alternatively, the pH sensitive detection component of the pharmaceutical composition may be a volatile and measurable biomolecule linked to the pharmaceutical composition by way of a pH-sensitive linkage. In one aspect, acetal pH-sensitive linkages are designed to undergo hydrolysis at mildly acidic pH (see, e.g., U.S. Pat. No. 7,348,453, which is incorporated herein by reference). Other labile linkages include, but are not limited to disulfide, acetal, ketal, enol ether, enol ester, amide, imine, imminium, enamine, silyl ether, silazane, and silyl enol ether bonds (see, e.g., U.S. Pat. No. 7,208,314). As such, a biomolecule may be linked to the pharmaceutical composition via a pH sensitive linkage. In a permissive pH range such as, for example, pH 5.0-6.0, the linkage may be broken and the biomolecule released. The released biomolecule may be exhaled by the subject and subsequently measured by a sensor associated with the method or device.

Pharmaceutical Composition with a Viral Homing Entity

Methods, compositions, and systems including the at least one pharmaceutical composition administered to a subject may be linked to a viral homing entity. The at least one pharmaceutical composition that includes one or more liposomes configured to achieve a selected pH of a pulmonary tissue in the subject may further include one or more viral homing entity. The viral homing entity may bind to a surface molecule of the virus. The viral homing entity may bind to a viral protein or proteins associated with the outer surface of the viral particle. Alternatively, the viral homing entity may bind to a cell or tissue of a subject that is either already virally infected or is susceptible to viral infection. Pulmonary epithelial cells are susceptible to viral infection and as such the viral homing entity may recognize and bind a protein or other biomolecule associated with the surface of pulmonary epithelial cells.

The viral homing entity may include, but is not limited to, at least a portion of an antibody, antibody-coated liposome, polynucleotide, polypeptide, receptor, viral plasmid, polymer, protein, toxin, lectin, or any combination thereof. The viral homing entity may recognize and bind to a protein or proteins associated with the outer surface of the viral particles. In one aspect, the viral homing entity may recognize and bind proteins associated with surface of influenza such as, for example, hemagglutinin (HA) and neuroaminidase (NA). Hemagglutinin plays an important role in recognition and binding to host cells as well as fusion of the virus with the host cell membrane. Hemagglutinin binds to α-sialosides on the target cell surface. Different viral hemagglutinins strictly recognize the difference in sialic acid-galactose linkage. Avian virus H3 subtype binds to avian receptor Neu5Ac(α2-3)Gal stronger than to human receptor Neu5Ac(α2-6)Gal. In contrast, neuraminidase (NA), a virus surface glycoprotein of influenza A and B viruses, cleaves the α-glycosidic linkages between sialic acid and the adjacent sugar and thus destroys virus receptors on the cell surface, extracellular inhibitors, and viral glycoproteins. The NA activity is believed to be particularly important at the late stages of infection by preventing hemagglutinin (HA)-mediated self-aggregation and facilitating release of progeny virions from cells. Interaction of virions with cell-associated and soluble sialylglycoconjugates of the host is mediated by HA and NA in an antagonistic manner, which has to be carefully balanced to allow efficient virus replication.

In some aspects, the viral homing entity may recognize and bind to a protein or proteins associated with other viruses associated with pulmonary infection. For example, the viral homing entity may recognize and bind to a protein or proteins associated with rhinovirus. Examples of proteins associated with the outer surface or capsid of rhinovirus include VP1, VP2, VP3, or VP4.

A viral homing entity that recognizes and binds to a viral protein may be an antibody or fragments thereof. Antibodies or fragments thereof for use as a viral homing entity may include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, or scFv antibodies. In one aspect, antibodies to influenza hemagglutinin may be generated using standard methods. Alternatively, antibodies to influenza hemagglutinin may be available from commercial sources (from, e.g., Santa Cruz Biotechnology, Inc., Santa Cruz, Calif.; Prosci, Inc., Poway, Calif.; United States Biological, Swampscott, Mass.). Similarly, antibodies to influenza neuroaminidase may be generated using standard methods or may be available from commercial sources (from, e.g., Genway Biotech, Inc., San Diego, Calif.; ABR Affinity Bioreagents, Golden Colo. (influenza B); Prosci, Inc., Poway, Calif.; GeneTex, Inc., San Antonio, Tex. (avian influenza).

Alternatively, the viral homing entity that recognizes and binds to a viral protein may be an aptamer. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure often termed "systematic evolution of ligands by exponential enrichment" (SELEX; see, e.g., Cao, et al., *Current Proteomics* 2:31-40, 2005; Proske, et al., *Appl. Microbiol. Biotechnol.* 69:367-374, 2005, which are incorporated herein by reference). In one aspect, aptamers that recognize and bind influenza A hemagglutinin may be constructed by screening a DNA library against a all or part of recombinant hemagglutinin using the SELEX method as described by Jeon, et al., *J. Biol. Chem.* 279:48410-48419, 2004, which is incorporated herein by reference.

The viral homing entity may be a biomolecule that is all or part of biomolecule that naturally binds to a virus. In an aspect, influenza hemagglutinin naturally binds α-sialosides on the target cell surface and as such the viral homing entity may include one or more α-sialosides. Similarly, rhinovirus interacts with ICAM-1 receptors on target cells and as such the viral homing entity may include all or part of ICAM-1. The viral homing entity may be a peptide. Novel peptides that bind selective targets may be generated using phage display methodologies (see, e.g., Spear, et al., *Cancer Gene Ther.* 8:506-511, 2001, which is incorporated herein by reference).

In some aspects, the viral homing entity may be a synthetic, small molecule compound that binds to a viral protein. In an aspect, a number of small molecule antiviral agents such as oseltamivir, zanamivir and peramivir bind to and inhibit the activity of influenza neuroaminidase. As such, the viral homing entity may constitute one or more antiviral agent either alone or conjugated to a carrier protein, for example.

In a further aspect, the viral homing entity may bind to a cell or cells in the pulmonary tissue of a subject that is either already virally infected or is susceptible to viral infection such as pulmonary epithelial cells. The viral homing entity may recognize a protein that is normally expressed on epithelial cells, e.g., Epithelial Membrane Antigen (MUC-1), Epithelial Specific Antigen (ESA), Epithelium-specific Cell Surface Glycoprotein, Epithelial Sodium Channels, Surfactant Protein, to name a few. Alternatively, the viral homing entity may recognize a protein on the surface of the target cell that is upregulated in response to the viral infection. In one aspect, rhinovirus induces expression of ICAM-1 on A549 lung epithelial cells and primary bronchial epithelial cells. ICAM1 is also a possible receptor for Rhinovirus. As such, an antibody to ICAM1 might be useful as a viral homing entity that binds to cells in the subject. Antibodies to ICAM1 are readily available from commercial sources.

Formulation of a Pharmaceutical Composition

Liquid Aerosol

The pharmaceutical composition may be formulated for inhalation administration as a liquid aerosol. In this instance, the one or more agent, e.g., one or more acidic, basic or buffering agent, may be dissolved into an appropriate solvent. Examples of appropriate solvents for inhalation include, but are not limited to water, alcohols, propylene glycol.

Dry Powder

The pharmaceutical composition including at least one agent to a pulmonary tissue of the subject, wherein the pharmaceutical composition is administered as two or more distinct and non-overlapping particle size ranges configured to contact two or more levels of pulmonary tissue of the subject may be formulated for inhalation administration as a dry powder. Formulating the pharmaceutical composition as a dry powder for inhalation may involve particle size reduction using jet milling, controlled precipitation, sieving, freeze-drying or spray-drying, for example. The pharmaceutical composition may be formulated in the absence of added excipients. Alternatively, the pharmaceutical composition may be formulated with added excipients. Examples of possible excipients for dry powder formulation for inhalation include, but are not limited to, lactose, dextran, mannitol, glucose, or a combination thereof. The pharmaceutical composition may also include surfactants such as oleic acid.

Liposomes

In another aspect, the pharmaceutical composition including at least one agent to a pulmonary tissue of the subject, wherein the pharmaceutical composition is administered as two or more distinct and non-overlapping particle size ranges configured to contact two or more levels of pulmonary tissue of the subject may be formulated for inhalation as part of a liposome. Dried phospholipids placed into an aqueous environment will spontaneously associate into multilamellar structures that function as permeability barriers. These lipid vesicles, termed liposomes, are composed of aqueous compartments separated from each other and the external medium by a series of closed concentric lipid bilayers. The composition of the aqueous compartments is the same as the medium in which the liposomes were formed; thus making it possible to entrap a wide variety of materials within the lipid bilayers.

The liposomes of the pharmaceutical composition as provided herein may be comprised of one or more of a variety of lipids. Suitable lipids include amphipathic lipids in which the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palm itoyloleoyl phosphatdylcholine, lysophosphatidylcholine, lysophosphatidylethanolamine, dipalmitoylphosphatidylcholine, dioleoylphosphatidylcholine, distearoylpliosphatidylcholine, or dilinoleoylphosphatidylcholine. Other phosphorus-lacking compounds, such as sphingolipids, glycosphingolipid families, diacylglycerols, and beta-acyloxyacids, may also be used. Additionally, such amphipathic lipids can be readily mixed with other lipids, such as triglycerides and sterols. Other bilayer-forming materials that may be used include long-chain dialkyl dimethyl ammonium compounds, for example di-stearyl dimethyl ammonium compounds such as di-stearyl dimethyl ammonium chloride, di-tallow dimethyl ammonium compounds such as di-tallow dimethyl ammonium chloride and mono- and dialkyl polyoxyethylene derivatives. Either a single phospholipid or a mixture of phospholipids may be used. Sterols, for example, cholesterol or ergosterol, may be added to the liposome to increase the stability of the liposomal bilayers and lipids possessing a positive or negative change, for example, phosphatidylethanolamine, gangliosides or phosphatic acid may be used to render the appropriate charge to the liposome and to increase the size of the aqueous compartments. Mixtures of lipids may be used to render the liposomes more fluid or more rigid and to increase or decrease permeability characteristics.

The liposomes of the pharmaceutical composition as provided herein may be prepared by a variety of methods including, but not limited to, hydration of lipid films, solvent injection, reverse-phase evaporation, sonication, extrusion, high pressure/homogenization, microfluidization, detergent dialysis, calcium-induced fusion of small liposome vesicles, and ether-infusion methods as described in, e.g., Szoka, et al., Ann. Rev. Biophys. Bioeng., 9:467, 1980; U.S. Pat. Nos. 4,186,183, 4,217,344, 4,235,871, 4,2619975, 4,485,054, 4,501,728, 4,774,085, 4,837,028, and 4,946,787; Deamer and Bangham, Biochim. Biophys. Acta, 443:629-634, 1976; Fraley, et al., Proc. Natl. Acad. Sci. USA, 76:3348-3352, 1979; Hope, et al., Biochim. Biophys. Acta, 812:55-65, 1985; Mayer, et al., Biochim. Biophys. Acta, 858:161-168, 1986; Williams, et al., Proc. Natl. Acad. Sci., 85:242-246, 1988; which are incorporated herein by reference. For example, liposomes may be formed from a lipid film dispersing a phospholipid or mixture of lipids in a suitable container in an organic solvent such as, ether, chloroform, or tert-butanol, and removing the organic solvent by methods such as evaporation, rotary evaporation under vacuum or lyophilization with commercially available freeze-drying equipment. Dispersing the resulting lipid film of dry lipid powder in an aqueous medium, e.g., distilled water, isotonic saline or buffered solutions, will result in the formation of liposomes. In this instance, the one or more agent of the pharmaceutical composition may be included in the aqueous medium during the formation of the liposomes to encapsulate the one or more agent of the pharmaceutical composition within the forming liposomes.

The liposomes of the pharmaceutical composition as provided herein may be administered to a subject by liquid aerosolization as a suspension in an appropriate aqueous medium. Alternatively, the liposomes of the pharmaceutical composition may be dried and micronized to one or more appropriate particle size either with or without added excipients and administered by dry powder inhalation.

Time or Extended Release Formulations

In some instances, the pharmaceutical composition as provided herein may be formulated for timed release or slow-absorbing. The pharmaceutical composition may be formulated for timed release using one or more of a combination of liposomes. The physiochemical properties of liposomes such as size, bilayer fluidity, surface charge, as well as the method of preparation, affect their in vivo behavior. The vesicle size and number of bilayers are key parameters in determining the residence time of liposomes. Small liposomes (≤0.1 μm), for example, are optimized by macrophages less rapidly and to a lesser extent than large liposomes (>0.1 μm) and therefore may have a longer half-life. Small liposomes also release their contents at a slower rate. It should be appreciated that formulation of small liposomes for liquid aerosol or dry powder inhalation, for example, may include generating two or more particle sizes that are preferably in the range of 1-10 μm for optimal delivery to the pulmonary tissue and as such each particle may itself contain multiple smaller liposomes encapsulating the one or more agents of the pharmaceutical composition.

Bilayer fluidity may also influence the behavior of the liposomes. In general, lipids have a characteristic phase transition temperature, existing in different physical states above and below this temperature. The phase transition temperature may range from −20° C. to 90° C. and is dependent upon the length and saturation of the fatty acid side chains. Below the phase transition temperature, the lipids are in a rigid, well-ordered arrangement. Above the phase transition temperature, lipids are in a liquid-crystalline state or fluid phase. As such, liposomes composed of lipids with a phase transition temperature above physiological temperature, e.g., above 37°

C., may be less fluid and hence less likely to leak their contents. As such, the fluidity of the liposome bilayer at various temperatures may be used to control release of liposome contents under physiological conditions.

Liposomes of the pharmaceutical composition may be further modified to modulate macrophage-dependent clearance of the liposomes from the pulmonary tissue and as such modulate residence. In one aspect, the liposomes of the pharmaceutical composition as provided herein may include a polymer surface coating such as polyethylene glycol (PEG) which helps the liposome evade recognition and uptake by the immune system and thus prolong residence time of the pharmaceutical composition in the lung of the subject.

In a further aspect, the pharmaceutical composition may include formulations which release the one or more agent from the two or more particle sizes based on the microenvironment of the pulmonary tissue. In one aspect, the pharmaceutical composition may include one or more liposome formulations in which release of the encapsulated contents of the liposome is pH-sensitive. The pharmaceutical composition may include polymer-caged liposomes in which preformed liposomes are treated with a cholesterol-functionalized poly (acrylic acid) additive, crosslinked, to become highly stable and have tunable pH-sensitive responses (see, e.g., Lee, et al., *J. Am. Chem. Soc.* 129:15096-15097, 2007, which is incorporated herein by reference). Additional examples of pH-sensitive liposomes are further described in Auguste, et al., *J. Control Release* [Epub ahead of print], 2008; U.S. Pat. Nos. 5,786,214, 5,965,434, 6,426,086, 6,897,196, 7,229,973, which are incorporated herein by reference.

Administration of a Pharmaceutical Composition

The pharmaceutical composition including at least one agent may be delivered by inhalation to a pulmonary tissue of the subject, wherein the pharmaceutical composition is administered as two or more distinct and non-overlapping particle size ranges configured to contact two or more levels of pulmonary tissue of the subject may be delivered by inhalation using a nebulizer. The nebulizer may be a jet nebulizer in which compressed gas (air or oxygen) passes through a narrow orifice creating an area of low pressure at the outlet of an adjacent liquid feed tube. The pharmaceutical composition in solution is drawn up from the fluid reservoir and shattered into droplets in the gas stream. Alternatively, the nebulizer may be an ultrasonic nebulizer in which a piezoelectric crystal vibrates at a high frequency and generates a fountain of liquid in the nebulizer chamber. In this instance, the higher the frequency of vibration, the small the droplet size.

The pharmaceutical composition as provided herein may be delivered by inhalation using a metered liquid inhaler which produces a fine aerosol in the respirable range by forcing the pharmaceutical composition solution through an array of nozzles. The pattern of holes in the nozzle as well as the size and geometry of each hole may be modified to generate droplets of a desired sized. These types of inhalers are exemplified by AERx (Aradigm, Hayward, Calif., USA), AeroDose (AeroGen, Sunnyvale, Calif., USA), and Respimat (Boehringer Ingelheim, Ingelheim, Germany).

The pharmaceutical composition may be delivered by inhalation using a metered-dose inhaler in which the pharmaceutical composition aerosol is driven by propellants, e.g., hydrofluoroalkanes. In some instances, the subject may manually actuate the inhaler followed by appropriate inhalation. Alternatively, the inhaler may be breath-actuated, firing in response to the subjects inspiratory effect.

Alternatively, the pharmaceutical composition may be delivered by inhalation using a dry powder inhaler. In this aspect, an aerosol of the pharmaceutical composition is created by directing air through loose powder. Dispersion of the powder into respirable particles depends on the creation of turbulent air flow within the powder container, causing aggregates to break up into particles small enough to be carried into the lower airways, if needed. The air flow may be generated by the subject. Alternatively, a battery driven propeller or compressed air may be used to aide in aerosolizing the powdered pharmaceutical composition.

In some instances, the pharmaceutical composition may be delivered directly to a subject using a personal nebulizer or inhaler as described herein. Alternatively, the pharmaceutical composition may be delivered to a subject or group of subjects in a room, building or other public space. For example, West describes a therapeutic air vent filter screen impregnated with a therapeutic agent for use in medicating the environment in a room (WIPO Patent WO/1999/030087, which is incorporated herein by reference). In some instances, the pharmaceutical composition including at least one agent to a pulmonary tissue of the subject, wherein the pharmaceutical composition is administered as two or more distinct and non-overlapping particle size ranges configured to contact two or more levels of pulmonary tissue of the subject may be delivered to a subject or group of subjects as a fine mist released into a room or other space, e.g., an elevator, bus, train or airplane cabin. The fine mist containing the pharmaceutical composition may be delivered through a ventilation system. Alternatively, the fine mist containing the pharmaceutical composition may be delivered from one or more devices situated in the space with the flow of mist directed towards a given subject or group of subjects. The delivery device may be incorporated into other objects in the room such as a computer screen or keyboard or a telephone receiver or seat back. Alternatively, the pharmaceutical composition may be delivered to a subject or group of subjects in a specially designed and enclosed area. In one aspect, a fine mist may be released into a small tent such as an oxygen tent.

The methods, compositions, and systems are further described with reference to the following examples; however, it is to be understood that the methods, compositions, and systems are not limited to such examples.

Illustrative Embodiments

Example 1

A method, composition, or system is provided for administering a pharmaceutical composition including at least one agent to a pulmonary tissue of a subject to modify the pH of the pulmonary tissue to prevent or treat a viral infection. A device may encompass the system as provided herein. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject for the prevention and treatment of a viral infection, for example, prevention and treatment of influenza viral infection. The first particle type of the pharmaceutical composition includes one or more agents at basic pH or a buffer that achieves a pH of greater than 7.0 in one portion of the respiratory tract. The second particle type of the pharmaceutical composition achieves a pH ranging from 6.4 to 7.4 in a second portion of the respiratory tract.

The binding and fusion of the human influenza virus with target cells in pulmonary tissue is affected by pH. The human influenza viral particles bind to the target cells through the interaction of viral hemagglutinin with sialylated cell surface receptors and are taken up by the target cell through the process of endocytosis. Hemagglutinin undergoes a conformational change at low pH and facilitates fusion of the viral particles with the target cells. Low pH also activates the influenza virus M2 protein ion channel which begins to pump protons across the viral membrane and lowering the internal viral pH which weakens protein-protein interactions between the viral matrix protein (M1) and the ribonucleoprotein (RNP) core, facilitating viral uncoating and replication. As such, increasing the pH in the pulmonary tissue may disrupt the normal viral infection process.

The pharmaceutical composition is administered as two or more distinct and non-overlapping particle size ranges configured to contact two or more levels of the pulmonary tissue and as such achieve two or more selected pH ranges in the two or more levels of the pulmonary tissue. In this manner, different pHs may be achieved in different portions of the lung. This may facilitate directed treatment of that portion of the lung that is infected by the virus while maintaining the microenvironment, e.g., a normal physiologic microenvironment, in other parts of the respiratory system. For example, human influenza A preferentially infects epithelial cells expressing 2-6-linked sialyl-galactosyl moieties which are prominent in tracheal and bronchial epithelial cells. The first particle type of the composition may include one or more agents that is basic in pH or is a buffer that achieves a pH of greater than 7.0 and is sized by milling, formulation or aerosolization to specifically deposit within regions of the upper airway, trachea and bronchus with a diameter, e.g., of about 3 to 6 μm. In contrast, the second particle type of the composition achieves a pH ranging from 6.4 to 7.4 and is sized by milling, formulation, or aerosolization to a smaller diameter that enables specific deposit within regions of the lower airway such as, for example, the bronchioles and alveoli with a diameter, e.g., of about 1 to 2 μm, to maintain a normal pH level.

Example 2

A method, composition, or system is provided for administering a pharmaceutical composition including at least one agent to a pulmonary tissue of a subject to modify the pH of the pulmonary tissue as a means of preventing or treating a viral infection. A device may encompass the system as provided herein. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject for the prevention and treatment of a viral infection. The first particle type of the pharmaceutical composition includes one or more agents that is acidic in pH or is a buffer that achieves a pH of less than 7.0 in one portion of the respiratory tract. The second particle type of the pharmaceutical composition achieves a pH ranging from 6.4 to 7.4 in a second portion of the respiratory tract.

Replication of human influenza and human rhinovirus may be affected by pH. For example, replication of human rhinoviruses may be reduced by 90% in the presence of acidic solutions such as, for example, citrate/phosphate buffer (pH 5.0), ascorbate (pH 5.0), or phthalate (pH 5.0) (see, e.g., Gem, et al., *J. Infect. Dis.* 195:1137-1143, 2007, which is incorporated herein by reference). Similarly, influenza viruses such as Influenza A Sydney/5/95 [H3N2], Influenza A Hong Kong/8/68 [H3N2] and avian reassortment virus A/Washington/897/80 X A Mallard/New York/6750/78 [H3N2] are rapidly inactivated in vitro by contact with acid buffered solutions at pH 3.5 (see, e.g., Rennie et al., *Respir. Res.* 8:38, 2007, which is incorporated herein by reference). In one aspect, lowering the pH in the pulmonary tissue may prevent or treat viral infection.

The pharmaceutical composition is administered as two or more distinct and non-overlapping particle size ranges configured to contact two or more levels of the pulmonary tissue and as such achieve two or more selected pH ranges in the two or more levels of the pulmonary tissue. In this manner, different pH ranges may be achieved in different portions of the lung. Treatment with the pharmaceutical composition may facilitate directed treatment of that portion of the lung that is infected by the virus while maintaining the microenvironment, e.g., a normal physiologic microenvironment, in other parts of the respiratory system. For example, human rhinovirus preferentially infects epithelial cells in the upper respiratory tract. In an aspect, the first particle type of the composition may include one or more agents at acidic pH or one or more agents as a buffer that achieves a pH of less than 7.0. The one or more agents may be sized by milling, formulation or aerosolization to specifically deposit within regions of the upper airway with a diameter, e.g., of about 4 to 6 μm. Examples of potential agents that are acid or acid buffers and may inhibit rhinovirus proliferation include, but are not limited to, acids such as acetic acid, ascorbic acid, citric acid, phytic acid, succinic acid, glutaric acid, phosphoric acid, or dilute hydrochloric acid, or other proton donors; and buffers such as citrate/phosphate buffer, ascorbate buffer, and phthalate buffer (see, e.g., Gem, et al., *J. Infect. Dis.* 195:1137-1143, 2007; Rennie, et al., *Respir. Res.* 8:38, 2007; Kuhrt, et al., *Antimicrob. Agents Chemother.* 26:924-927, 1984). In contrast, the second particle type of the composition achieves a pH ranging from 6.4 to 7.4 and is sized by milling, formulation, or aerosolization to a smaller diameter, e.g., a diameter of about 1 to 3 μm that enables specific deposit within regions of the lower airway, for example, in the bronchioles and alveoli to maintain a normal pH level.

Example 3

A method, composition, or system is provided for administering a pharmaceutical composition including at least one agent to a pulmonary tissue of the subject based on receiving and or sensing data regarding an environmental condition, e.g., a potentially infectious environment. A device may encompass the system as provided herein. The potentially infectious environment may be determined based on direct measurement, inferred based on time and location, and or provided based on data from one or more agencies involved in pathogen surveillance. The data regarding the potentially infectious environment may be acquired prior to the subject entering that environment. In response to a potentially infectious environment, the pharmaceutical composition may be self-administered or automatically administered to the subject. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

The potentially infectious environment may be determined based on direct measurement. Airborne pathogens such as viral particles, for example, may be detected by recovering the particles in or on a collection medium (liquid, semisolid, or solid substrate, for example) using an impinger, filters, bubblers, or impactors, for example, and then assaying the substrate for the presence of the targeted virus using an appropriate assay system. Real time polymerase chain reaction (RT-PCR) amplification may be used to determine the presence and identity of viruses. For example, Chen, et al., describe using real-time PCR to detect the avian H5N1 influenza virus (Chen et al., *J. Med. Microbiol.* 56:603-607, 2007). Alternatively, airborne pathogens may be detected using some form of microsensor.

Alternatively, a potentially infectious environment may be inferred from the time of year and global location. For example, flu season or that portion of the year in which there are regular outbreaks of influenza infections usually occurs in the cold half of the year in each hemisphere. Alternatively, data regarding a potentially infectious environment may be received by the subject from an agency tracking viral infection in a given location. Such an agency includes, but is not limited to, a local Public Health authority, the Center for Disease Control (CDC), the World Health Organization (WHO) or similar agencies in a given location. Both the CDC and WHO actively tract outbreaks of avian H5N1 influenza. The location of the potentially infectious environment may be the current location of the subject. Alternatively, the location of the potentially infectious environment may be a location or locations to which the subject will be traveling to in the near future.

Information regarding a potentially infectious environment is sent to a subject or group of subjects. Alternatively, the information regarding a potentially infectious environment is sent to a third party individual or individuals such as a physician or other caregiver. Upon receiving and/or sensing data regarding a potentially infectious environment, a component of the device, e.g., a sensor, may analyze the incoming data and determine that administration of the pharmaceutical composition is appropriate under the current or predicted conditions. In one aspect, the device may automatically administer the pharmaceutical composition. Alternatively, the device may inform a subject and/or third party caregiver of the current or predicted conditions and the subject and/or third party caregiver may choose to administer the pharmaceutical composition.

The pharmaceutical composition is administered as two or more distinct and non-overlapping particle size ranges configured to contact two or more levels of the pulmonary tissue and achieve two or more selected pH ranges in the two or more levels of the pulmonary tissue. In this manner, different pHs may be achieved in different portions of the lung and may facilitate directed treatment of that portion of the lung that is infected by the virus while maintaining the microenvironment in other parts of the respiratory system. For example, avian H5N1 influenza virus preferentially infects cells expressing the 2-3-linked siayly-galactosyl moieties and infects a different portion of the human lung relative to infection by human influenza virus. Based on analysis of autopsied human lung tissue, avian H5N1 influenza preferentially infects human Type II pneumocytes found deep in the lower respiratory tract (see, e.g., Uiprasertkul, et al., *Emerging Infectious Dis.* 11: 1036-1041, 2005, which is incorporated herein by reference). The first particle type of the composition may include one or more agents that is basic in pH or is a buffer that achieves a pH of greater than 7.0, for example, and is sized by milling, formulation or aerosolization for deposition into the alveolar spaces with a diameter of about 1 μm. In contrast, the second particle type of the composition achieves a pH ranging from 6.4 to 7.4 and is sized by milling, formulation, or aerosolization to a larger diameter of about 5 μm for deposition in the upper and conducting airways to maintain a normal pH level.

Example 4

A method, composition, or system is provided for administering a pharmaceutical composition including at least one agent to a pulmonary tissue of the subject based on sensing data regarding a physiological condition of the subject such as, for example, the current pH of the pulmonary tissue. A device may encompass the system as provided herein. The pH of the pulmonary tissue of a subject may be modified by the pharmaceutical composition to achieve a selected pH range to prevent or treat a viral infection. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

The methods, compositions, and systems includes one or more sensors that are configured to monitor a physiological condition of the subject, e.g., the pulmonary pH of the subject. The pulmonary pH of a subject may be measured in the expired breath condensate, which consists, in part, of aerosolized particles from the airway lining fluid, water vapor condensation, and water soluble volatile gases. The one or more sensors are configured to monitor the pH of the expired breath condensate as an indicator of the pH of the pulmonary tissue. The one or more sensors may be further configured to monitor at least one of humidity of an exhalant, temperature, breathing rate, peak rate of exhalation, tidal volume, vital capacity, inspiratory capacity, expiratory reserve volume, or residual volume.

The one or more sensors in the method or device for monitoring pH in the expired breath condensate may be sufficiently small to be semi-permanently located in a segment of the airway of a subject. Alternatively, the sensors may be incorporated into a dental or nasal prosthesis or into a piece of jewelry, e.g., a nose or tongue piercing. Alternatively, the sensors for monitoring pH may be incorporated into a mask or other covering of the mouth and/or nose that is worn by the subject. The mask may be worn at all times, and will monitor expired breath condensate of a subject continuously and in real time. Alternatively, the mask may be worn temporarily to monitor a subject's expired breath condensate at any given point in time.

The pharmaceutical composition is administered automatically in response to the sensed data regarding the current pH of the pulmonary tissue of a subject. Alternatively, the pharmaceutical composition is self-administered using an inhaler, for example, by the subject in response to the sensed data regarding the current pH of the pulmonary tissue of a subject. The pharmaceutical composition is administered as two or more distinct and non-overlapping particle size ranges configured to contact two or more levels of the pulmonary tissue and as such achieve two or more selected pH ranges in the two or more levels of the pulmonary tissue. The particle sizes and pH ranges selected are dependent upon the type of virus that has been encountered or is expected to be encountered and the relative location of the infection of that virus within the respiratory tract as described herein.

Example 5

A method, composition, or system is provided for administering a pharmaceutical composition including at least one agent to a pulmonary tissue of the subject, wherein the pharmaceutical composition includes one or more viral homing entities. A device may encompass the system as provided herein. The one or more viral homing entities directs the pharmaceutical composition to a specific location. The specific location may be a viral particle and or a targeted host cell of the subject. The one or more viral homing entities associated with the pharmaceutical composition may bind to a surface molecule of the virus. Alternatively, the one or more viral homing entities associated with the pharmaceutical composition may bind to a cell or tissue of a subject that is either already infected with a virus or is susceptible to viral infection. The pharmaceutical composition is administered as two or more distinct and non-overlapping particle size ranges configured to contact two or more levels of pulmonary tissue of the subject, wherein the at least one agent is configured to achieve a selected pH range in the two or more levels of pulmonary tissue of the subject.

The pharmaceutical composition administered to a subject may be linked to one or more viral homing entities. The viral homing entity may bind to a surface molecule of the virus, for example, a viral protein or proteins associated with the outer surface of the viral particle. Examples of viral surface proteins include, but are not limited to influenza A hemagglutinin and neuraminidase and rhinovirus capsid proteins VP1, VP2, VP3, and VP4. Alternatively, the viral homing entity may bind to a cell or cells in the pulmonary tissue of a subject that is either already virally infected or is susceptible to viral infection such as, for example, pulmonary epithelial cells. The viral homing entity may recognize a protein that is normally expressed epithelial cells, e.g., Epithelial Membrane Antigen (MUC-1), Epithelial Specific Antigen (ESA), Epithelium-specific Cell Surface Glycoprotein, Epithelial Sodium Channels, Surfactant Protein, to name a few. Alternatively, the viral homing entity may recognize a protein on the surface of the target cell that is upregulated, for example, in response to the viral infection. In one aspect, rhinovirus may induce increased expression of intercellular adhesion molecule (ICAM-1) in primary bronchial epithelial cells.

The viral homing entity may be at least a portion of an antibody or fragments thereof, antibody-coated liposome, polynucleotide, polypeptide, receptor, viral plasmid, polymer, protein, toxin, lectin, or any combination thereof that specifically binds to either one or more viral surface protein or one or more target cells or combinations thereof. In one aspect, the viral homing entity may be a commercially available antibody to hemagglutinin (from, e.g., Santa Cruz Biotechnology, Inc., Santa Cruz, Calif.; Prosci, Inc., Poway, Calif.; United States Biological, Swampscott, Mass.). In another aspect, the viral homing entity may be a biomolecule that naturally interacts with one or more components of a viral particle or the target cells. The viral homing entity may consist of one or more $\alpha$-sialosides that specifically interact with influenza hemagglutinin. Alternatively, the viral homing entity may be a peptide. Novel peptides that bind selective targets may be generated using phage display methodologies (see, e.g., Spear, et al., *Cancer Gene Ther.* 8:506-511, 2001, which is incorporated herein by reference). In some aspects, the viral homing entity may be a synthetic, small molecule compound that binds to a viral protein. Examples of small molecule inhibitors include, but are not limited to, antiviral agents oseltamivir, zanamivir and peramivir that interact with influenza neuroaminidase.

The pharmaceutical composition is administered as two or more distinct and non-overlapping particle size ranges configured to contact two or more levels of the pulmonary tissue and as such achieve two or more selected pH ranges in the two or more levels of the pulmonary tissue. One or more of the distinct particle sizes of the pharmaceutical composition may be modified with the viral homing entity. The particle sizes and pH ranges selected are dependent upon the type of virus that has been encountered or is expected to be encountered and the relative location of the infection of that virus within the respiratory tract as described herein. The particle size configured to target that part of the respiratory tract likely to be involved in viral infection may be selectively modified with the one or more viral homing entity to enhance targeting of that portion of the pharmaceutical composition to the infection site.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The herein described components (e.g., steps), devices, and objects and the description accompanying them are used as examples for the sake of conceptual clarity and that various configuration modifications using the disclosure provided herein are within the skill of those in the art. Consequently, as used herein, the specific exemplars set forth and the accompanying description are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable", to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:

a pharmaceutical composition including at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject; and an aerosol generator configured to generate an aerosol dose of the pharmaceutical composition, the aerosol generator being operably coupled to at least one of a heating, ventilation, or air conditioning system to allow delivery of at least a portion of the aerosol dose of the pharmaceutical composition therethrough.

2. The system of claim 1, wherein the at least one agent includes at least one buffering agent.

3. The system of claim 2, wherein the at least one buffering agent includes at least one of a phosphate buffer, a citrate buffer, a lactate buffer, a pyruvate buffer, or an organic acid buffer.

4. The system of claim 1, wherein the at least one agent includes at least one basic agent.

5. The system of claim 4, wherein the at least one basic agent includes an anion.

6. The system of claim 5, wherein the anion includes at least one of phosphate, citrate, lactate, or pyruvate.

7. The system of claim 1, wherein the at least one agent includes at least one acidic agent.

8. The system of claim 1, wherein the pharmaceutical composition includes a first agent in first-sized particles configured to maintain a first pH range in a first level of pulmonary tissue of the subject, and a second agent in second-sized particles configured to maintain a second pH range in a second level of pulmonary tissue of the subject.

9. The system of claim 8, wherein the first-sized particles and the second-sized particles include the two or more particle size ranges of from about 6 μm to less than about 10 μm, from about 4 μm to about 6 μm, from about 2 μm to about 4 μm, or from about 1 μm to about 2 μm.

10. The system of claim 8, wherein at least one of the first-sized particles and the second-sized particles have the particle size ranges which include from about 3 μm to about 4 μm, from about 2 μm to about 3 μm, from about 1 μm to about 2 μm, from about 1 μm to about 1500 nm, from about 800 nm to about 1 micron, from about 700 nm to about 800 nm, from about 600 nm to about 700 nm, from about 500 nm to about 600 nm, from about 400 nm to about 500 nm, from about 300 nm to about 400 nm, from about 200 nm to about 300 nm, from about 100 nm to about 200 nm, from about 75 nm to about 100 nm, from about 50 nm to about 75 nm, or from about 1 nm to about 50 nm.

11. The system of claim 8, wherein at least one of the first-sized particles and the second-sized particles have the particle size ranges which include from about 1800 nm to about 1900 nm, from about 1700 nm to about 1800 nm, from about 1600 nm to about 1700 nm, from about 1500 nm to about 1600 nm, from about 1400 nm to about 1500 nm, from about 1300 nm to about 1400 nm, from about 1200 nm to about 1300 mm, from about 1100 nm to about 1200 nm, from about 1000 nm to about 1100 nm, from about 900 nm to about 1000 nm, from about 800 nm to about 900 nm, from about 700 nm to about 800 nm, from about 600 nm to about 700 nm, from about 500 nm to about 600 nm, from about 400 nm to about 500 nm, from about 300 nm to about 400 nm, from about 250 nm to about 300 nm, from about 200 nm to about 250 nm, from about 100 nm to about 200 nm, from about 75 nm to about 100 nm, from about 50 nm to about 75 nm, or from about 1 nm to about 50 nm.

12. The system of claim 8, wherein the first agent includes a buffering agent to maintain the first pH range below approximately 7.0.

13. The system of claim 8, wherein the first agent is a buffering agent configured to maintain the first pH range from approximately 7.2 to approximately 7.6.

14. The system of claim 8, wherein the second agent is a buffering agent configured to maintain the second pH range from approximately 6.4 to approximately 7.4.

15. The system of claim 1, wherein the system includes a device including the aerosol generator and the pharmaceutical composition.

16. The system of claim 1, wherein the aerosol generator is configured to administer the pharmaceutical composition in response to a sensed condition of the subject.

17. The system of claim 1, wherein the pharmaceutical composition is administered in response to a sensed environmental condition including a potentially infectious environment.

18. The system of claim 1, wherein the pharmaceutical composition is configured to be administered orally or intranasally.

19. The system of claim 1, wherein the pharmaceutical composition is configured to provide a timed-release of the at least one agent.

20. The system of claim 1, wherein the pharmaceutical composition is configured to provide an extended release form of the at least one agent.

21. The system of claim 1, wherein the at least one agent is linked to a viral homing entity.

22. The system of claim 21, wherein the viral homing entity binds to a surface molecule of the virus.

23. The system of claim 21, wherein the viral homing entity binds to a cell or tissue of the subject.

24. The system of claim 1, wherein the aerosol generator includes at least one of a vaporizer, a nebulizer, or an atomizer.

25. The system of claim 7, wherein the at least one acidic agent includes a cation.

26. The system of claim 25, wherein the cation includes at least one of $H^+$, $K^+$, or $Mg^{2+}$.

27. The system of claim 1, wherein the aerosol generator is configured to administer the pharmaceutical composition to the pulmonary tissue of the subject.

28. The system of claim 1, further comprising a sensor configured to monitor a condition of the subject.

29. The system of claim 28, wherein the sensor is configured to monitor at least one of pH of the pulmonary tissue or pH of an exhalant.

30. The system of claim 29, further comprising a pH-sensitive detection component configured to communicate to the pH-monitoring sensor.

31. The system of claim 30, wherein the pH-sensitive detection component releases a marker indicating a pH range, and the pH-monitoring sensor is configured to recognize the marker.

32. The system of claim 30, wherein the pharmaceutical composition including the at least one agent is administered in response to information from the pH-sensitive detection component.

33. The system of claim 28, wherein the sensor is configured to monitor at least one of humidity of an exhalant, temperature, breathing rate, peak rate of exhalation, tidal volume, vital capacity, inspiratory capacity, expiratory reserve volume, or residual volume.

34. The system of claim 28, further comprising a controller responsive to the sensor that is configured to selectively deliver one or more particle size ranges.

35. The system of claim 34, wherein the controller is configured to deliver one or more particle size ranges of the selected pH.

36. The system of claim 28, wherein the monitoring sensor is in an airway passage of the subject.

37. The system of claim 36, wherein the monitoring sensor is in a sinus or a nostril of the subject.

38. The system of claim 28, wherein the monitoring sensor is integral with the system.

39. The system of claim 1, wherein the pulmonary tissue includes epithelial tissue, mesenchymal tissue, or endothelial tissue.

40. The system of claim 1, wherein the at least one agent is configured to achieve a selected pH range in two or more levels of oropharynx or nasopharynx tissue.

41. The system of claim 1, wherein the at least one agent is configured to achieve a selected pH range in two or more levels of tracheal tissue.

42. The system of claim 1, wherein the levels of pulmonary tissue include bronchial, bronchiole, alveolar duct, or alveoli tissue.

43. The system of claim 1, wherein the aerosol generator is configured to administer the pharmaceutical composition orally or nasally.

44. The system of claim 1, wherein the aerosol generator administers a continuous or pulsatile dose of the pharmaceutical composition.

45. The system of claim 1, wherein an aerosol dose of the pharmaceutical composition is configured to be delivered to one or more individuals in a man-made enclosed space.

46. The system of claim 1, wherein the pharmaceutical composition is configured to provide a timed-release of an ion.

47. The system of claim 1, wherein the pharmaceutical composition is configured to provide an extended release of an ion.

48. The system of claim 1, wherein the pharmaceutical composition is a liquid or a powder.

49. The system of claim 1, wherein the subject is mammalian or avian.

50. A system comprising:

a pharmaceutical composition including at least one agent configured as two or more distinct and non-overlapping particle size ranges configured to contact two or more levels of pulmonary tissue of a subject, wherein the at least one agent is configured to achieve a selected pH range in the two or more levels of pulmonary tissue of the subject; and an aerosol generator configured deliver the pharmaceutical composition to the subject or a group of subjects in a man-made enclosed area, the aerosol generator being incorporated into at least one of a computer screen, a keyboard, a telephone receiver, or a seat back.

51. The system of claim 1, wherein the enclosed area is at least one of a room, building, elevator, bus, train, or airplane cabin.

* * * * *

UNITED STATES PATENT AND TRADEMARK OFFICE

CERTIFICATE OF CORRECTION

PATENT NO. : 8,584,670 B2
APPLICATION NO. : 12/319654
DATED : November 19, 2013
INVENTOR(S) : Roderick A. Hyde et al.

It is certified that error appears in the above-identified patent and that said Letters Patent is hereby corrected as shown below:

In the Claims:

Column 34, line 56, claim 51:

"51. The system of claim 1, wherein the enclosed area..." should read:
--51. The system of claim 50, wherein the enclosed area...--

Signed and Sealed this
Nineteenth Day of August, 2014

Michelle K. Lee
*Deputy Director of the United States Patent and Trademark Office*